US012618795B2

(12) United States Patent
Roy

(10) Patent No.: US 12,618,795 B2
(45) Date of Patent: May 5, 2026

(54) METHODS FOR ASYMMETRIC SEMI-NESTED ISOTHERMAL NUCLEOTIDE AMPLIFICATION

(71) Applicant: SEEK LABS, INC., Salt Lake City, UT (US)

(72) Inventor: Anindita Roy, Salt Lake City, UT (US)

(73) Assignee: SEEK LABS, INC., Salt Lake City, UT (US)

( * ) Notice: Subject to any disclaimer, the term of this patent is extended or adjusted under 35 U.S.C. 154(b) by 732 days.

(21) Appl. No.: 17/715,894

(22) Filed: Apr. 7, 2022

(65) Prior Publication Data

US 2022/0325337 A1      Oct. 13, 2022

Related U.S. Application Data

(60) Provisional application No. 63/240,227, filed on Sep. 2, 2021, provisional application No. 63/183,504, filed on May 3, 2021, provisional application No. 63/171,761, filed on Apr. 7, 2021.

(51) Int. Cl.

| | |
|---|---|
| *G01N 27/327* | (2006.01) |
| *B01D 29/05* | (2006.01) |
| *B01D 29/58* | (2006.01) |
| *B01D 39/16* | (2006.01) |
| *C12N 9/12* | (2006.01) |
| *C12N 15/10* | (2006.01) |
| *C12Q 1/6806* | (2018.01) |
| *C12Q 1/6853* | (2018.01) |
| *C12Q 1/70* | (2006.01) |
| *C25F 1/00* | (2006.01) |

(52) U.S. Cl.
CPC ......... *G01N 27/3276* (2013.01); *B01D 29/05* (2013.01); *B01D 29/58* (2013.01); *B01D 39/16* (2013.01); *C12N 9/1252* (2013.01); *C12N 15/1017* (2013.01); *C12Q 1/6806* (2013.01); *C12Q 1/6853* (2013.01); *C12Q 1/701* (2013.01); *C25F 1/00* (2013.01); *C12Q 2600/166* (2013.01)

(58) Field of Classification Search
CPC .... G01N 27/3276; B01D 29/05; B01D 29/58; B01D 39/16; C12N 9/1252; C12N 15/1017; C12Q 1/6853; C12Q 1/701; C12Q 2600/166; C12Q 1/6825; C25F 1/00
See application file for complete search history.

(56) References Cited

U.S. PATENT DOCUMENTS

| | | | |
|---|---|---|---|
| 6,503,711 B1 | 1/2003 | Krull et al. | |
| 6,609,618 B2 | 8/2003 | Colpan | |
| 7,264,927 B2 | 9/2007 | Nargessi et al. | |
| 8,367,334 B2 | 2/2013 | Pugh et al. | |
| 8,598,338 B2 | 12/2013 | Bair et al. | |
| 9,238,809 B2 | 1/2016 | Khripin et al. | |
| 9,540,635 B2 | 1/2017 | Ruegg et al. | |
| 9,637,777 B2 | 5/2017 | Seul et al. | |
| 9,696,328 B2 | 7/2017 | Hansen et al. | |
| 10,392,655 B2 | 8/2019 | Boutell et al. | |
| 10,550,425 B2 | 2/2020 | Sampas et al. | |
| 10,704,087 B2 | 7/2020 | Satterfield | |
| 11,180,787 B2 | 11/2021 | Eboigbodin et al. | |
| 2004/0191801 A1 | 9/2004 | Heeger et al. | |
| 2007/0009925 A1 | 1/2007 | Fang et al. | |
| 2007/0154922 A1 | 7/2007 | Collier et al. | |
| 2008/0283741 A1 | 11/2008 | Mukaibatake | |
| 2014/0080726 A1* | 3/2014 | Prakash | C12Q 1/6837 |
| | | | 506/9 |
| 2017/0096694 A1 | 4/2017 | Eboigbodin et al. | |
| 2017/0152549 A1 | 6/2017 | Shih et al. | |
| 2017/0198279 A1 | 7/2017 | Loper et al. | |
| 2017/0233791 A1 | 8/2017 | Spier et al. | |
| 2017/0362636 A1* | 12/2017 | Rajagopal | C12Q 1/686 |
| 2019/0376130 A1 | 12/2019 | Nobile et al. | |
| 2020/0149030 A1 | 5/2020 | Hillebrand et al. | |
| 2020/0200693 A1 | 6/2020 | Boyanov et al. | |
| 2020/0391198 A1 | 12/2020 | Yi | |
| 2021/0010065 A1 | 1/2021 | Salk et al. | |

FOREIGN PATENT DOCUMENTS

| | | |
|---|---|---|
| CN | 102671487 A | 9/2012 |
| EP | 0585660 B1 | 9/1994 |
| WO | 2003040687 A2 | 5/2003 |
| WO | 2004094635 A2 | 4/2004 |

(Continued)

OTHER PUBLICATIONS

Francois, Patrice, et al. "Robustness of a loop-mediated isothermal amplification reaction for diagnostic applications." FEMS Immunology & Medical Microbiology 62.1 (2011): 41-48 (Year: 2011).*
Mason, Michael Glenn, and José Ramón Botella. "A simple, robust and equipment-free DNA amplification readout in less than 30 seconds." RSC advances 9.42 (2019): 24440-24450. (Year: 2019).*
Mayboroda, Olena, et al. "Isothermal solid-phase amplification system for detection of Yersinia pestis." Analytical and bioanalytical chemistry 408 (2016): 671-676. (Year: 2016).*
Meyer, Ralph R., and Phyllis S. Laine. "The single-stranded DNA-binding protein of *Escherichia coli*." Microbiological reviews 54.4 (1990): 342-380. (Year: 1990).*
Zhang, Zw. et al. (2005). Sensitive Detection of SARS Coronavirus by a Novel Asymmetric Multiplex Nested RT-PCR Amplification Coupled With Oligonucleotide Microarray Hybridization. In: Joos, T.O., Fortina, P. Methods in Molecular Medicine. Humana Press. (Year: 2005).*

(Continued)

*Primary Examiner* — Cynthia B Wilder
(74) *Attorney, Agent, or Firm* — Wilson Sonsini Goodrich & Rosati

(57) ABSTRACT

Aspects of the present disclosure relate to methods, compositions, and systems for asymmetric semi-nested isothermal nucleotide amplification (ANINA) for the amplification of single-stranded oligonucleotides. In some aspects, the methods, compositions, and systems herein do not require thermal melting and may be used in a point-of-need setting. In some aspects, the methods feature amplification of a target region and production of single stranded amplicons including the target region.

27 Claims, 6 Drawing Sheets

(56) References Cited

FOREIGN PATENT DOCUMENTS

| | | | |
|---|---|---|---|
| WO | 2005118847 | A1 | 12/2005 |
| WO | 2015022359 | A1 | 2/2015 |
| WO | 2015185655 | A1 | 12/2015 |
| WO | 2016041591 | A1 | 3/2016 |
| WO | 2016144192 | A1 | 9/2016 |
| WO | 2017218777 | A1 | 12/2017 |
| WO | 2018195594 | A1 | 11/2018 |

OTHER PUBLICATIONS

Yongxi Zhao, Feng Chen, Qian Li, Lihua Wang, and Chunhai Fan Isothermal Amplification of Nucleic Acids. Chemical Reviews 2015 115 (22), 12491-12545. DOI: 10.1021/acs.chemrev.5b00428. pp. 12493-12520. (Year: 2015).*

Mitani, Y., Lezhava, A., Kawai, Y., Kikuchi, T., Oguchi-Katayama, A., Kogo, Y., Itoh, M., Miyagi, T., Takakura, H., Hoshi, K. and Kato, C., 2007. Rapid SNP diagnostics using asymmetric isothermal amplification and a new mismatch-suppression technology. Nature Methods, 4(3), pp. 257-262. (Year: 2007).*

Satterfield, Brent C. "Cooperative Primers: 2.5 Million-Fold Improvement in the Reduction of Nonspecific Amplification." The Journal of Molecular Diagnostics 16.2 (2014): 163-173.

Wong, Ian Y., and Nicholas A. Melosh. "An electrostatic model for DNA surface hybridization." Biophysical journal 98.12 (2010): 2954-2963.

Xia, Xuhua. "The effect of probe length and GC% on microarray signal intensity: characterizing the functional relationship." Int J Syst Synthetic Biol 1.2 (2010): 171-183.

Binder et al. "Mismatch and G-stack modulated probe signals on SNP microarrays." PLoS One 4.11 (2009): e7862.

Gu et al. "Single molecule profiling of molecular recognition at a model electrochemical biosensor." Journal of the American Chemical Society 140.43 (2018): 14134-14143.

Kudlicki, Andrzej S. "G-quadruplexes involving both strands of genomic DNA are highly abundant and colocalize with functional sites in the human genome." PloS one 11.1 (2016): e0146174.

Yang et al. "Evidence for the direct interaction between methylene blue and guanine bases using DNA-modified carbon paste electrodes." Electroanalysis: An International Journal Devoted to Fundamental and Practical Aspects of Electroanalysis 14.18 (2002): 1299-1302.

Rohs et al. "Methylene blue binding to DNA with alternating GC base sequence: a modeling study." Journal of the American Chemical Society 122.12 (2000): 2860-2866.

Pereira et al. "An efficient method for genomic DNA extraction from different molluscs species." International journal of molecular sciences 12.11 (2011): 8086-8095.

Mason et al. "Rapid (30-second), equipment-free purification of nucleic acids using easy-to-make dipsticks." Nature protocols 15.11 (2020): 3663-3677.

Zou et al. "Nucleic acid purification from plants, animals and microbes in under 30 seconds." PLoS biology 15.11 (2017): e2003916.

Mason et al. "A simple, robust and equipment-free DNA amplification readout in less than 30 seconds." RSC advances 9.42 (2019): 24440-24450.

* cited by examiner

Asymmetric semi-Nested INA (ANINA) primer sequences based on Target Region

TSBR

TSBR

METHODS FOR ASYMMETRIC SEMI-NESTED ISOTHERMAL NUCLEOTIDE AMPLIFICATION

CROSS-REFERENCES TO RELATED APPLICATIONS

This application is a non-provisional and claims benefit of U.S. Provisional Application No. 63/171,761 filed Apr. 7, 2021 and U.S. Provisional Application No. 63/240,227 filed Sep. 2, 2021, the specification(s) of which is/are incorporated herein in their entirety by reference.

This application is a non-provisional and claims benefit of U.S. Provisional Application No. 63/183,504 filed May 3, 2021, the specification of which is incorporated herein in their entirety by reference.

FIELD OF THE INVENTION

The present invention features an asymmetric semi-nested isothermal nucleotide amplification (ANINA) method, as well as compositions and systems, for the amplification of single-stranded oligonucleotides from a target sequence.

BACKGROUND OF THE INVENTION

Nucleic acid testing (NAT) biosensing technologies, such as those employing the use of fluorophores or redox sensors or other physicochemical detectors, are currently used in numerous applications for the detection of nucleic acids (NA) of a particular pathogen or mutated genes in an organism. NATs use the specificity and sensitivity afforded by nucleic acid base pairing to detect different NA sequences, sometimes differing by a single nucleotide. However, for a NAT to work effectively, single-stranded DNA and/or RNA need to be isolated for detection. This allows for a physicochemical detector (e.g., a genosensor probe) to hybridize to its complementary sequence, which should be a single-stranded DNA and/or RNA target.

This can be achieved by fragmenting the genomic DNA/RNA or by amplifying the target sequence using nucleic acid amplification technologies (NAATs), which increases the number of target copies and the sensitivity of the detection. However, both of the aforementioned methods have shortcomings associated with them.

First, fragmenting DNA in a controlled manner to a size between 25-100 bps is extremely difficult to achieve. Most mechanical and chemical breakdown methods give ~1 kbps fragments which are not preferred as longer sequences are more difficult to denature and tend to form secondary structures, thereby decreasing the hybridization efficiency. Additionally, enzymatic methods usually use DNAses that have a propensity of depolymerizing DNA to fragments less than 25 bps. Even the commercially available DNAses, such as fragmentase (NEB), are difficult to control to give size-specific fragments. Lastly, the nucleic acid fragments need to be denatured, if they are double-stranded, to bind to the single-stranded probe, leading to competition between the probe and homologous strand which makes the process more complicated and inefficient. Furthermore, there is the potential for non-specific binding to the probe of other fragments.

The most used NAAT is PCR which remains the gold standard of current diagnostics. However, PCR is difficult to conduct in a point-of-need setting, because of the requirement of specific cycling temperatures: for example, (i) a very high temperature (usually 95° C.) required for thermal melting of dsDNA/dsRNA (either the starting sequence or the amplicons after the first amplification cycle), (ii) annealing temperature (usually between 50-70° C.) for the primers to bind to, and (iii) the extension temperature for the corresponding amplification by the common polymerases (e.g., Taq (72° C.)). Additionally, PCR and real-time PCR are limited to the time required for each cycle, thereby increasing the total time of the reactions. Other isothermal NAATs, such as LAMP (loop-mediated isothermal amplification), HDA (helicase-dependent isothermal DNA amplification), SDA (strand displacement amplification), NASBA (nucleic acid sequence-based amplification), RCA (rolling circle amplification), can amplify DNA in a simpler setting by avoiding the need for a cycling method. However, all the aforementioned methods still require either thermal melting of the dsDNA or dsRNA, or incubation at a temperature higher than 50° C. or require the addition of finicky nucleases adding to the complexity of the process.

Additionally, most NAATs can amplify if there is a contamination, and therefore nested amplification strategies are utilized to make the amplicon results more specific. Furthermore, most NAATs utilize a dual strand amplification strategy to increase the number of copies exponentially. However, this results in dsDNA amplicons, which still need to be denatured before being detected. While asymmetric amplification strategies can be used to amplify mostly single-stranded DNA, it heavily limits the amplification rate to a linear rate instead of the exponential rate of the dual-strand approach.

Currently, an isothermal cost-effective nucleic acid amplification technology (NAAT) that specifically amplifies single-strand oligonucleotides is needed. Furthermore, a method that does not require thermal melting and can be done in a point-of-need setting would be ideal.

BRIEF SUMMARY OF THE INVENTION

It is an objective of the present invention to provide systems, compositions, and methods (e.g., asymmetric semi-nested isothermal nucleotide amplification (ANINA)) that allow for amplifying single-stranded oligonucleotides. Embodiments of the present invention can be freely combined with each other if they are not mutually exclusive.

The present invention features a method of real time asymmetric semi-nested isothermal nucleotide amplification (ANINA) for producing and quantifying single-stranded oligonucleotide amplicons. The method comprises introducing to a sample a set of primers, e.g., three primers. e.g., a first primer, a second primer, and a third primer. FIG. 1A, FIG. 1B, and FIG. 3 outlines the origin of the sequences of the primers and their relationship to the target region. In some embodiments, the first primer refers to a first forward primer (FP1), the second primer refers to a second forward primer (FP2), and the third primer refers to a reverse primer (RP). In some embodiments, the first primer refers to a first reverse primer (RP1), the second primer refers to the second reverse primer (RP2), and the third primer refers to the forward primer (FP). Thus, as used herein, the first forward primer is also known as the first primer, and the second forward primer is also known as the second primer, and the reverse primer is also known as the third primer. As used herein, the first reverse primer is also known as the first primer, the second reverse primer is also known as the second primer, and the forward primer is also known as the third primer.

In some embodiments, the ratio of the first primer (P1): second primer (P2):third primer (P3) (e.g., FP1:FP2:RP or RP1:RP2:FP) is (1-10):(10-200):(1-10). In some embodiments, the ratio of P1:P2:P3 is 1:(50-100):3.

In some embodiments, the method comprises introducing to a sample a solution comprising one or more enzymes, dNTPs, one or more buffering reagents, one or more salts, and one or more crowding reagents and a reporter probe. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the RP and a sequence extending from and including at least a portion of the FP2. In other embodiments, the method produces single-stranded oligonucleotide amplicons according to a sequence comprising at least a portion of a complementary sequence of the FP and a sequence extending from and including at least a portion of the RP2. In some embodiments, the method quantifies the single-stranded oligonucleotide amplicons produced when the single-stranded oligonucleotide amplicons bind to the reported probe.

The present invention features a method of asymmetric semi-nested isothermal nucleotide amplification (ANINA) for producing single-stranded oligonucleotide amplicons. In some embodiments, said method comprises introducing to a sample 1) a set of primers comprising a first forward primer (FP1), a second forward primer (FP2), and a reverse primer (RP). In some embodiments. FP2 is downstream of FP1 In other embodiments, said method comprises introducing to a sample 1) a set of primers comprising a first reverse primer (RP1), a second reverse primer (RP2), and a forward primer (FP). In some embodiments, RP2 is upstream of RP1. In some embodiments, the ratio of P1:P2:P3 (e.g., FP1:FP2:RP and/or RP1:RP2:FP) is 1:(50-100):3. In some embodiments, the ratio of P1:P2:P3 (e.g., FP1:FP2:RP and/or RP1:RP2:FP) is (1-10):(10-200):(1-10). In some embodiments, the method comprises introducing to a sample 2) a solution comprising enzymes, dNTPs. and a buffer comprising a buffering agent, salts, and crowding reagents. In some embodiments, the method comprises incubating the sample with the primers and the solution at a reaction temperature for a length of time. In some embodiments, the method produces single-stranded oligonucleotide amplicons according to a sequence comprising at least a portion of a complementary sequence of the RP and a sequence extending from and including at least a portion of the FP2. In other embodiments, the method produces single-stranded oligonucleotide amplicons according to a sequence comprising at least a portion of a complementary sequence of the FP and a sequence extending from and including at least a portion of the RP2.

In some embodiments, the present invention features a method of point-of-care amplification of a target sequence. In some embodiments, said method comprises introducing to a sample 1) a set of primers comprising a first forward primer (FP1), a second forward primer (FP2), and a reverse primer (RP). In some embodiments, FP2 is downstream of FP1. In other embodiments, said method comprises introducing to a sample 1) a set of primers comprising a first reverse primer (RP1), a second reverse primer (RP2), and a forward primer (FP). In some embodiments, RP2 is upstream of RP1. In some embodiments, the ratio of P1:P2: P3 (e.g., FP1:FP2:RP and/or RP1:RP2:FP) is 1:(50-100):3. In other embodiments, the ratio of P1:P2:P3 (e.g., FP1:FP2: RP and/or RP1:RP2:FP) is (1-10):(10-200):(1-10). In some embodiments, said method comprises introducing to a sample 2) a solution comprising enzymes, dNTPs. and a buffer comprising a buffering agent, salts, and crowding reagents. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the RP and a sequence extending from and including at least a portion of the FP2. In other embodiments, the method produces single-stranded oligonucleotide amplicons according to a sequence comprising at least a portion of a complementary sequence of the FP and a sequence extending from and including at least a portion of the RP2.

In some embodiments, the present invention features a kit for amplifying single-stranded oligonucleotides. In some embodiments, said kit comprises: a recombinase, a single-stranded binding protein, strand displacing polymerase, dNTPs, and a buffer. In some embodiments, the buffer comprises buffering agents, salts, and crowding reagents. In some embodiments, said kit comprises: a first primer (P1), a second primer (P2), and a third primer (P3), e.g., a first forward primer (FP1), a second forward primer (FP2), wherein FP2 is downstream from FP1, and a reverse primer (RP) or a first reverse primer (RP1), a second reverse primer (FP2), wherein RP2 is upstream from RP1, and a forward primer (FP). In some embodiments, the ratio of P1:P2:P3 (e.g., FP1:FP2:RP and/or RP1:RP2:FP) is 1:(50-100):3. In other embodiments, the ratio of P1:P2:P3 (e.g., FP1:FP2:RP and/or RP1:RP2:FP) is (1-10):(10-200):(1-10). In some embodiments, the kit further comprises a reverse transcriptase enzyme.

The present invention features a system for performing asymmetric semi-nested isothermal nucleotide amplification (ANINA) for producing single-stranded oligonucleotide amplicons as described herein. In some embodiments, said system comprises: a kit for amplifying single-stranded oligonucleotides as described herein and a reaction chamber for accepting the kit and a sample. In some embodiments, the reaction chamber is configured to incubate the kit and sample at a reaction temperature for a length of time such that the asymmetric semi-nested isothermal nucleotide amplification (ANINA) system amplifies a single-stranded amplicon therein.

One of the unique and inventive technical features of the present invention is the use of a first forward primer (FP1), a second forward primer (FP2), wherein FP2 is downstream from FP1, and a reverse primer (RP) or the use of a first reverse primer (RP1), a second reverse primer (RP2) wherein RP2 is upstream from RP1, and a forward primer (FP1) in addition to the use of a specific ratio of the forward primers to reverse primer for each primer set. Additionally, the primer design process is similar to that of PCR, instead of complicated methods used for other INAs, such as LAMP, RCA, SIBA. The semi-nested approach also increases the specificity of the amplification over a non-nested approach, while the specific ratio of the primers increases the amplification rate of the single strand target region compared to traditional asymmetric amplification strategies. Additionally. In this system there is no need for ATP or ATP-γ-S or an additional ATP regeneration system for the ATPases such as recombinase, such as those required in recombinase polymerase amplification (RPA) or strand invasion based amplification (SIBA). Without wishing to limit the invention to any theory or mechanism, it is believed that the technical feature of the present invention advantageously provides for a method of producing mostly single-stranded oligonucleotide amplicons. None of the presently known prior references or work has the unique inventive technical feature of the present invention.

Furthermore, the inventive technical features of the present invention contributed to a surprising result. For example, the present invention features an amplification system that did not need a separate addition of ATP or ATP-γ-S. While additional dATP helped with the amplification, amplification without the need of addition of any dATP, apart from the dATP already present in the dNTP mix was also observed. Additionally, the methods and systems described herein can be combined with a NAT platform which uses a sensitive detection technology, and can detect the amplicons in real time. This can translate to give information about not only the presence of a specific target gene or gene polymorphisms, but the amount of the said target as well.

In some embodiments, this method can also be combined with any other system that requires a specific amplification of a single-stranded oligonucleotide target for detection or a part of another experiment, such as gene silencing. In other embodiments, this method can be expanded for multiplex amplification of multiple target sequences.

As previously discussed, the present invention features methods of asymmetric semi-nested isothermal nucleotide amplification for producing single-stranded oligonucleotide amplicons of a target region of nucleic acid. In some embodiments, the method comprises introducing to a sample a set of primers and a solution comprising enzymes, dNTPs, and a buffer comprising buffering reagents, salts, and crowding reagents, and incubating the sample with the primers and solution at a reaction temperature for a length of time. The set of primers may comprise a first primer (P1), P1 has a sequence that is a set of nucleotides 5' to the target region, wherein P1 binds to a first complementary binding region (CSBR1) which is on a strand opposite the target region; a second primer (P2), P2 has a sequence that is a set of nucleotides (a) 5' to the target region or (b) 5' to the target region and including a portion of the target region, wherein P2 binds to a second complementary binding region (CSBR2) which is on a strand opposite the target region; wherein the set of nucleotides for P1 is at least partially 5' to the set of nucleotides for P2; and a third primer (P3), P3 has a sequence that is a set of nucleotides complementary to (a) at least a portion of the target region, or (b) a portion of the 3' end of the target region and one or more nucleotides downstream of the 3' end of the target region; or (c) an area 3' to the target region; wherein P3 binds to a target strand binding region (TSBR) of the target strand. The ratio of P1:P2:P3 may be (1-10):(20-200):(1-20). The method produces single-stranded oligonucleotide amplicons having a sequence comprising at least the target region.

In some embodiments, the ratio of P1:P2:P3 is 1:(50-100):3. In some embodiments, the target region is from 20 to 500 bases in length. In some embodiments, the buffer further comprises a reducing agent. In some embodiments, the enzymes comprise a recombinase enzyme, a single strand binding protein, a strand displacing polymerase, a reverse transcriptase or a combination thereof. In some embodiments, the recombinase is RecA, or Rad51, or RadA. In some embodiments, the single-stranded binding protein is *Escherichia col* single-stranded DNA binding protein (EcSSB). In some embodiments, the strand displacing polymerase is *Bacillus subtilis* DNA polymerase I (Bsu), or mesophilic DNA polymerase. In some embodiments, the buffering reagents are Tris, PBS, or a combination thereof. In some embodiments, the salts comprise sodium chloride (NaCl), potassium chloride (KCl), magnesium chloride (MgCl$_2$), sodium acetate (NaCH$_3$COO), magnesium acetate (Mg(C$_2$H$_2$O$_2$)$_2$, monosodium phosphate (NaH2PO4), disodium phosphate (NA$_2$PO$_4$), or a combination thereof. In some embodiments, the crowding agent is polyvinylpyrrolidone (PVP), or polyethylene glycol (PEG), Ficoll, Dextran, or a combination thereof. In some embodiments, the reaction temperature ranges from 15° C. to 60° C. In some embodiments, the length of time is from 5 to 60 minutes. In some embodiments, the buffer has a pH ranging from 7.0-8.0. In some embodiments, the method further comprises detecting the target sequence. In some embodiments, detection of the target sequence features introducing a genosensor probe.

The present invention also features methods of real time asymmetric semi-nested isothermal nucleotide amplification (ANINA) for producing and quantifying single-stranded oligonucleotide amplicons of a target region of nucleic acid. In some embodiments, the method comprises introducing to a sample a set of primers, a solution comprising enzymes, dNTPs, and a buffer comprising buffering reagents, salts, and crowding reagents; and a reporter probe; and incubating the sample with the primers and solution at a reaction temperature for a length of time. In some embodiments, the set of primers comprises a first primer (P1), P1 has a sequence that is a set of nucleotides 5' to the target region, wherein P1 binds to a first complementary binding region (CSBR1) which is on a strand opposite the target region; a second primer (P2), P2 has a sequence that is a set of nucleotides (a) 5' to the target region or (b) 5' to the target region and including a portion of the target region, wherein P2 binds to a second complementary binding region (CSBR2) which is on a strand opposite the target region; wherein the set of nucleotides for P1 is at least partially 5' to the set of nucleotides for P2; and a third primer (P3), P3 has a sequence that is a set of nucleotides complementary to (a) at least a portion of the target region, or (b) a portion of the 3' end of the target region and one or more nucleotides downstream of the 3' end of the target region; or (c) an area 3' to the target region; wherein P3 binds to a target strand binding region (TSBR) of the target strand. In some embodiments, the ratio of P1:P2:P3 is (1-10):(20-200):(1-20). The method produces single-stranded oligonucleotide amplicons having a sequence comprising at least the target region. The method may quantify the single-stranded oligonucleotide amplicons produced when the single-stranded oligonucleotide amplicons bind to the reported probe.

In some embodiments, the one or more enzymes comprises a recombinase enzyme, a strand displacing polymerase, a reverse transcriptase, or a combination thereof, in some embodiments, the recombinase enzyme is RecA. In some embodiments, the strand displacing polymerase is *Bacillus subtilis* DNA polymerase I (Bsu), Bst, or Klenow Fragment. In some embodiments, the buffering reagents are Tris, PBS, or a combination thereof. In some embodiments, the one or more salts is magnesium acetate (Mg(C$_2$H$_2$O$_2$)$_2$ or (Mg(C$_2$H$_2$O$_2$)$_2$ and one or a combination of: sodium chloride (NaCl), potassium chloride (KCl), magnesium chloride (MgCl$_2$), sodium acetate (NaCH$_2$COO), monosodium phosphate (NaH$_2$PO$_4$), and disodium phosphate (Na$_2$PO$_4$). In some embodiments, the one or more crowding reagents comprises polyvinylpyrrolidone (PVP) or PVP and one or a combination of: polyethylene glycol (PEG), Ficoll, and Dextran. In some embodiments, the solution further comprises a single stranded binding protein (SSB). In some embodiments, the SSB is T4 gp32 SSB, *E. coli* SSB (EcSSB), or *Bacillus subtilis* DNA polymerase I (Bsu). In some embodiments, the solution further comprises a reducing agent. In some embodiments, the sample is in a buffer comprising 20 mM PBS, 2.5 mM EDTA, and 0.05% SDS.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1A shows a representation of the sequences for the asymmetric semi-Nested INA (ANINA) primers relative to a target region (of a dsDNA template), wherein the target region is the sequence to be amplified. The target sequence can be either in the sense or antisense strand. As shown, the sequence for the first primer and the second primer are the same as particular nucleotides upstream of (or 5 to) the target region. The first primer is upstream of (or 5' to) the second primer; both are upstream (generally) of the target region. In some embodiments, the first primer and second primer overlap, e.g., the last nucleotide (or the last 2+ nucleotides) of the first primer are the same as the first nucleotide (or first 2+ nucleotides) of the second primer. In some embodiments, the second primer and target region overlap, e.g., the last nucleotide (or last 2+ nucleotides) of the second primer are the same as the first nucleotide of the first 2+ nucleotides of the target region. Thus, the first primer binds to a first complementary region of the strand opposite the strand of the target region, and the second primer binds to a second complementary region of the strand opposite the strand of the target region. The sequence for the third primer is that of nucleotides on the strand complementary to the target region and upstream of and/or overlapping with the complementary nucleotides of the target region. e.g., the third primer will bind to the target region and/or nucleotides downstream of the target region. In some embodiments, the ratio of the primers is Primer1:Primer2:Primer3=1:(50-100): 3, e.g. 10 nM:1 uM:30 nM.

FIG. 1B shows binding of the first primer to a first complementary strand binding region (CSBR1) and the third primer binding to the target strand binding region (TSBR). The first primer binds to the strand opposite the strand of the target region, and the third primer binds to the strand with the target region. Note the terms CSBR1 and TSBR are for clarification purposes only so as to describe what strand and/or nucleotides the primers bind.

FIG. 1C shows binding of the second primer to a second complementary strand binding region (CSBR2) and the third primer binding to the target strand binding region (TSBR). The second primer binds to the strand opposite the strand of the target region, and the third primer binds to the strand with the target region. Note the terms CSBR2 and TSBR are for clarification purposes only so as to describe what strand and/or nucleotides the primers bind.

Figure 2:
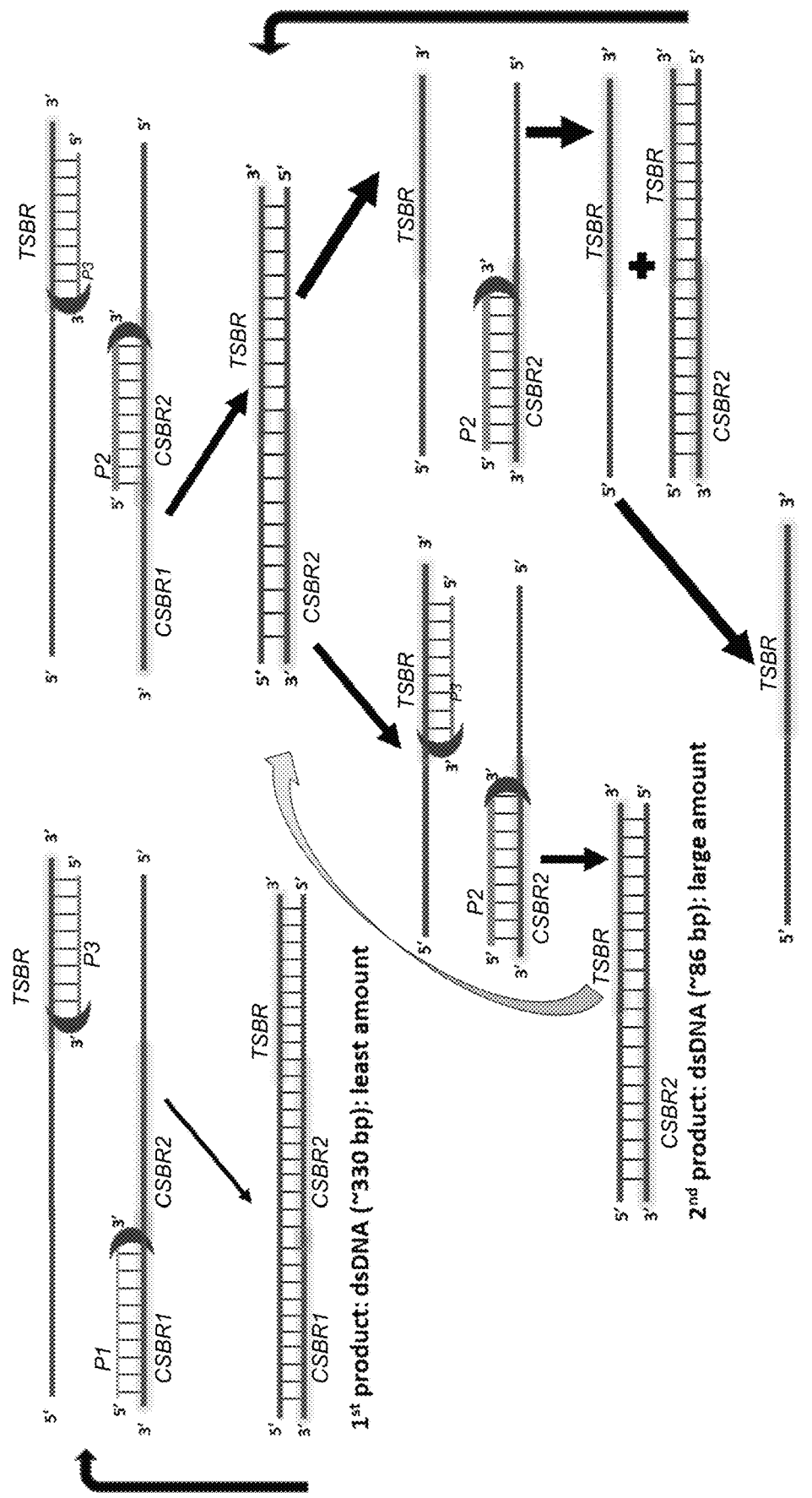
FIG. 2 shows the asymmetric semi-Nested INA (ANINA) strategy.
Figure 3:
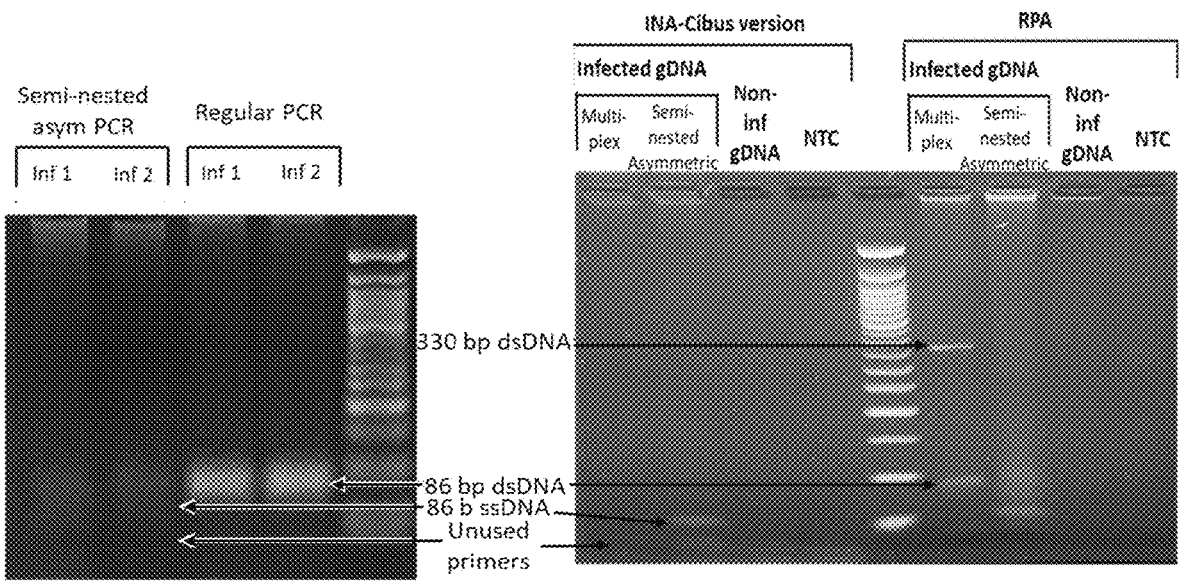
FIG. 3 shows the asymmetric, semi-Nested Isothermal Nucleotide Amplification (ANINA) method is able to detect single-stranded amplicons from an infected animal.
Figure 4:
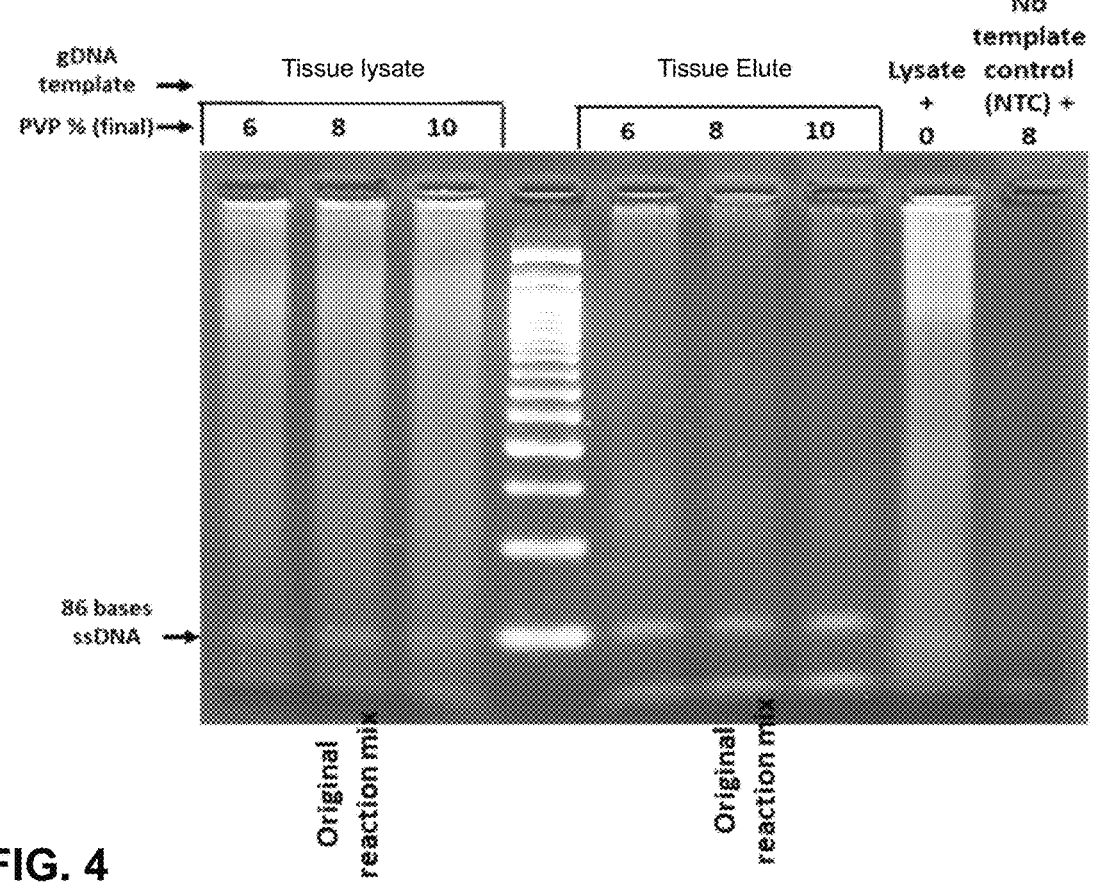
FIG. 4 shows the ANINA optimization using cell tissue lysate and elution and increasing the percent of PVP (a crowding agent).
Figure 8:
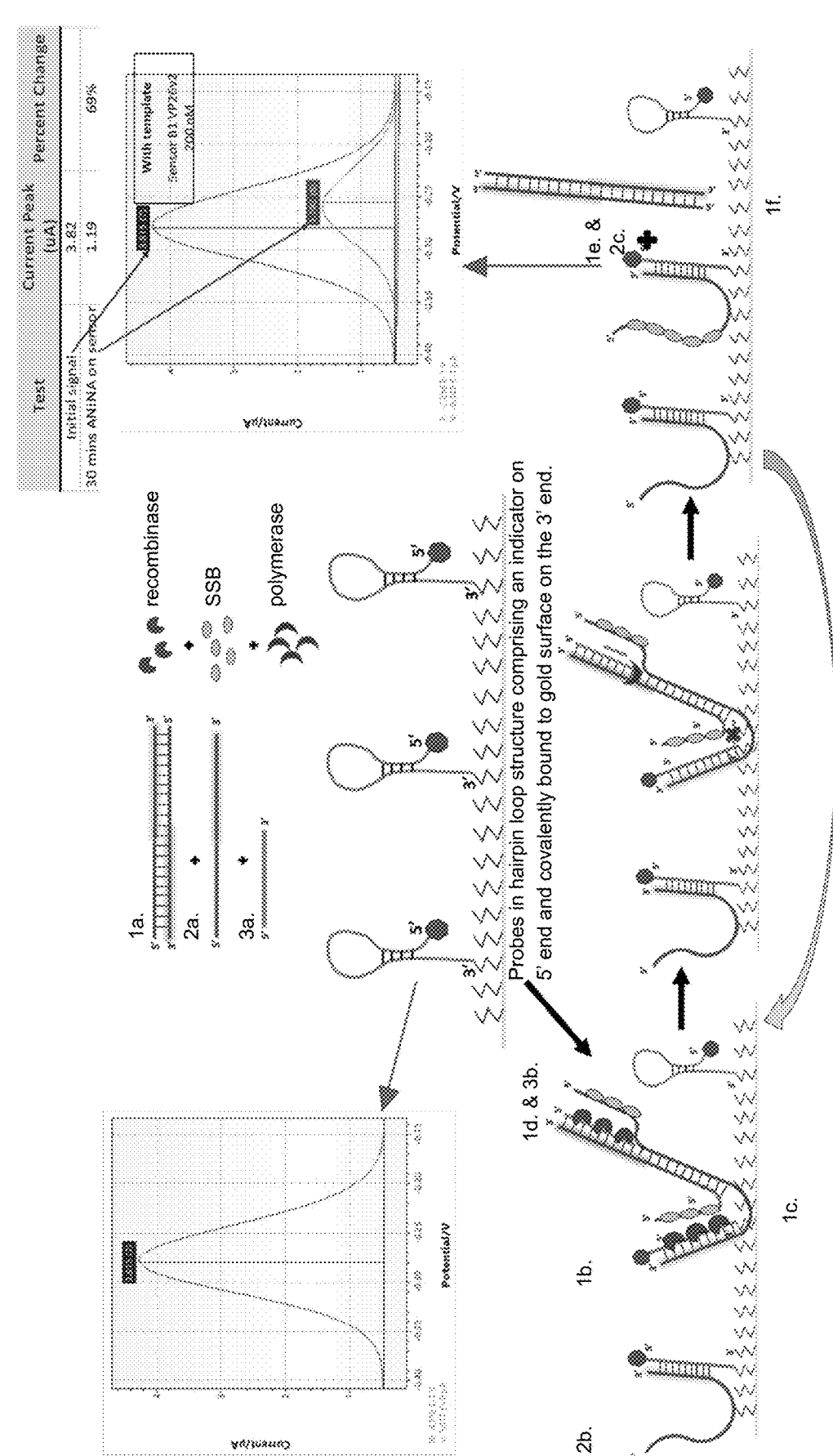

FIG. 8, shows an example of a reaction that may proceed in a solution comprising a first primer (P1), a second primer (P2), a third primer (P3) in a ratio as described herein (i.e. ANINA ratios), enzymes, and genomic nucleotides (e.g., gDNA or gRNA). The final signal will depend on the amount of primers added and target nucleotides (e.g., gDNA/RNA) present. 1a, a DNA section from the genomic region containing target region. 2a. ANINA ssDNA amplicon, containing the electrochemical probe's target region in green, made in solution (as shown in FIG. 2), after the P1 and P2 are used up; 3a. P2 (present in highest concentration in ANINA primer ratio); 1b. The ssDNA probe is complementary to the target region, therefore RecA-bound probe can bind the target region and open up the genomic DNA; 2b. The ssDNA ANINA amplicons from solution reaction can bind to the probe directly. 1c. The probe is bound to gold on the 3' side, thus being blocked, so the polymerase cannot use the probe as a primer. 1d. & 3b. The RecA-bound Primer 2 binds to the other strand) of the genomic DNA and starts amplifying, leading to amplification of the Primer 2, which creates a new dsDNA target amplicon and frees up the other strand which stays bound to the probe. 1e, and 2c. The bound probe removes the methylene blue away from the surface, leading to a decrease in signal that can be measured. 1f. The new dsDNA amplicon starts a new cycle.

DETAILED DESCRIPTION OF THE INVENTION

Before the present compounds, compositions, and/or methods are disclosed and described, it is to be understood that this invention Is not limited to specific synthetic methods or to specific compositions, as such may, of course, vary. It is also to be understood that the terminology used herein is for the purpose of describing particular embodiments only and is not intended to be limiting.

For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

Referring now to the figures, the present invention features systems, compositions, and methods (e.g., real-time asymmetric semi-nested isothermal nucleotide amplification (ANINA)) that allows for amplifying single-stranded oligonucleotides.

Figure 1A:
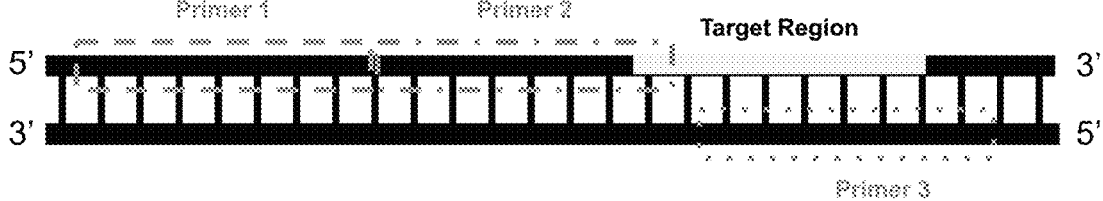
Figure 1B:
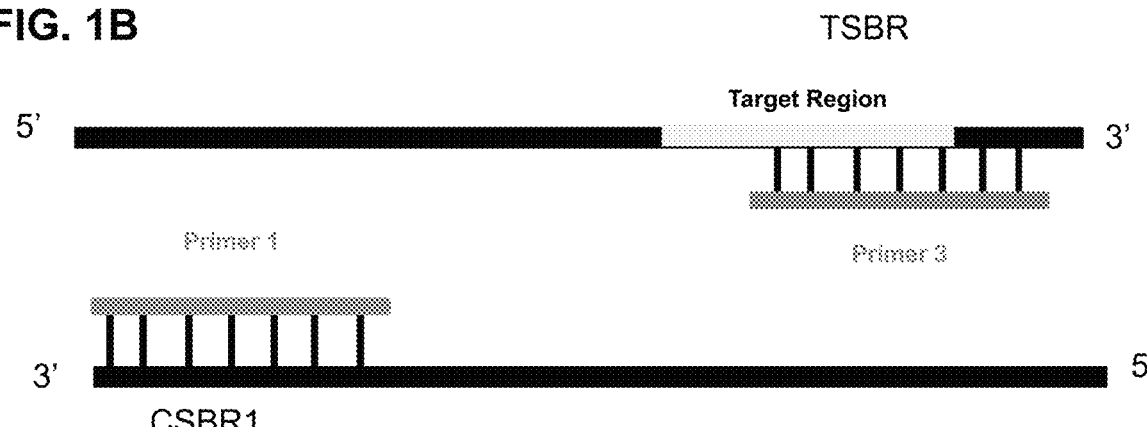
Figure 1C:
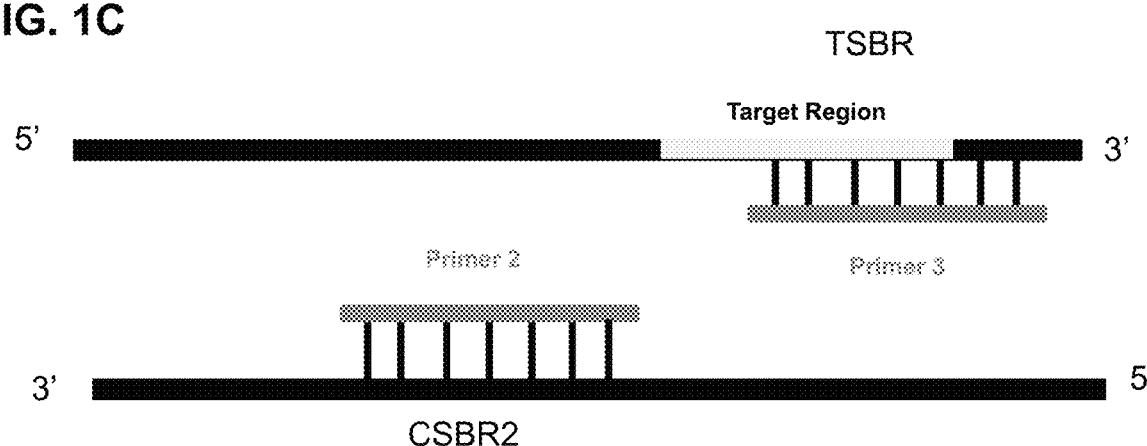

FIG. 1A, FIG. 1B, and FIG. 1C outlines the origin of the sequences of the primers and their relationship to the target region. In some embodiments, the first primer refers to a first forward primer (FP1), the second primer refers to a second forward primer (FP2), and the third primer refers to a reverse primer (RP). In some embodiments, the first primer refers to a first reverse primer (RP1), the second primer refers to the second reverse primer (RP2), and the third primer refers to the forward primer (FP). Thus, as used herein, the first forward primer is also known as the first primer, and the second forward primer is also known as the second primer, and the reverse primer is also known as the third primer. As used herein, the first reverse primer is also known as the first primer, the second reverse primer is also known as the second primer, and the forward primer is also known as the third primer.

In some embodiments, the first primer (P1) and second primer (P2) share similar nucleotides e.g., the 3' end (e.g., the last nucleotide, the last two, the last three, last four, last five, etc.) of P1 is the same as the 5' end (the first nucleotide, the first two, the first three, first four, first five, etc.) of P2. In some embodiments, the first primer (P1) and second primer (P2) do not overlap. In some embodiments, the first primer (P1) and second primer (P2) are spaced a distance apart. e.g., the sequences are from two regions of the strand that are at least 1 nucleotide apart, e.g., 1 nucleotide apart, 2, 3, 4, 5, 6, 7, 8, 9, 10, more than 10, 11, 12, 13, 14, 15, 16, 17, 18, 19 20, 21, 22, 23, 24, 25, 25, 30, 30-40, 40-50, 50-75, 75-80, 80-100, 100-150, 150-200, more than 200, etc.

In some embodiments, the second primer (P2) and the target region share similar nucleotides e.g., the 3' end (e.g., the last nucleotide, the last two, the last three, etc.) of P2 is the same as the 5' end (the first nucleotide, the first two, the first three, etc.) of the target region. In some embodiments, the second primer (P2) and the target region do not overlap. In some embodiments, the second primer (P2) and the target region are spaced a distance apart. e.g., the sequences are from two regions of the strand that are at least 1 nucleotide apart, e.g., 1 nucleotide apart, 2, 3, 4, 5, 6, 7, 8, 9, 10, 11, 12, 13, 14, 15, 18, 17, 18, 19 20, 21, 22, 23, 24, 25, 25-30, 30-40, 40-50, 50.75, 75-80, 80-100, 100-150, 150-200, more than 200, etc.

In some embodiments, the third primer (P2) and the nucleotides complementary to the target region share similar nucleotides e.g., the 3' end (e.g., the last nucleotide, the last two, the last three, etc.) of P3 is the same as the 5' end (the first nucleotide, the first two, the first three, etc.) of the nucleotides complementary to the target region. In some embodiments, the third primer (P3) and the nucleotides complementary to the target region do not overlap. In some embodiments, the third primer (P3) and the nucleotides complementary to the target region are spaced a distance apart, e.g., the sequences are from two regions of the strand that are at least 1 nucleotide apart, e.g., 1 nucleotide apart, 2, 3, 4, 5, 6, 7, 8, 9, 10, 11, 12, 13, 14, 15, 16, 17, 18, 19 20, 21, 22, 23, 24, 25, 25-30, 30-40, 40-50, 50-75, 75-80, 80-100, 100-150, 150-200, more than 200, etc.

In some embodiments, the target region is from 20 to 500 bases in length. In other embodiments, the target region is from 20 to 400 bases in length. In some embodiments, the target region is from 20 to 300 bases in length. In some embodiments, the target region is from 20 to 200 bases in length. In some embodiments, the target region is from 20 to 100 bases in length. In some embodiments, the target region is from 20 to 50 bases in length. In some embodiments, the target region is from 20 to 25 bases in length. In some embodiments, the target region is from 25 to 500 bases in length. In some embodiments, the target region is from 25 to 400 bases in length. In some embodiments, the target region is from 25 to 300 bases in length. In some embodiments, the target region is from 25 to 200 bases in length. In some embodiments, the target region is from 25 to 100 bases in length. In some embodiments, the target region is from 25 to 50 bases in length. In some embodiments, the target region is from 50 to 500 bases in length. In some embodiments, the target region is from 50 to 400 bases in length. In some embodiments, the target region is from 50 to 300 bases in length. In some embodiments, the target region is from 50 to 200 bases in length. In some embodiments, the target region is from 50 to 100 bases in length.

FIG. 2 outlines the strategy of the methods hereon. For example, as shown on the left side of FIG. 2, the first primer (P1) and third primer (P3) bind to the complementary strand and target strand, respectively, the first primer (P1) binds to the first complementary strand binding region (CSBR1) and the third primer (P3) binds to the target strand binding region (TSBR). As shown on the right side of FIG. 2, the second primer (P2) and third primer (P3) bind to the complementary strand and target strand, respectively; the second primer (P2) binds to the second complementary strand binding region (CSBR2) and the third primer (P3) binds to the target strand binding region (TSBR). The products are shown below. As the reactions proceed, the longest product of dsDNA is produced in the least amount (left side of FIG. 2), and the shorter products are produced in greater amounts relative to the longest product; the highest yield is the single stranded oligonucleotide amplicon generated by P2 and P3 (see bottom of FIG. 2). This contains the target region and includes the target strand binding region. Note the sizes listed in FIG. 2 are examples only. The present invention is not limited to an 88 base amplicon.

In some embodiments, the single-stranded oligonucleotide amplicons are from 20 to 500 bases in length. In other embodiments, the single-stranded oligonucleotide amplicons are from 20 to 400 bases in length. In some embodiments, the single-stranded oligonucleotide amplicons are from 20 to 300 bases in length. In some embodiments, the single-stranded oligonucleotide amplicons are from 20 to 200 bases in length. In some embodiments, the single-stranded oligonucleotide amplicons are from 20 to 100 bases in length. In some embodiments, the single-stranded oligonucleotide amplicons are from 20 to 50 bases in length. In some embodiments, the single-stranded oligonucleotide amplicons are from 20 to 25 bases in length. In some embodiments, the single-stranded oligonucleotide amplicons are from 25 to 500 bases in length. In some embodiments, the single-stranded oligonucleotide amplicons are from 25 to 400 bases in length. In some embodiments, the single-stranded oligonucleotide amplicons are from 25 to 300 bases in length. In some embodiments, the single-stranded oligonucleotide amplicons are from 25 to 200 bases in length. In some embodiments, the single-stranded oligonucleotide amplicons are from 25 to 100 bases in length. In some embodiments, the single-stranded oligonucleotide amplicons are from 25 to 50 bases in length. In some embodiments, the single-stranded oligonucleotide amplicons are from 50 to 500 bases in length. In some embodiments, the single-stranded oligonucleotide amplicons are from 50 to 400 bases in length. In some embodiments, the single-stranded oligonucleotide amplicons are from 50 to 300 bases in length. In some embodiments, the single-stranded oligonucleotide amplicons are from 50 to 200 bases in length. In some embodiments, the single-stranded oligonucleotide amplicons are from 50 to 100 bases in length.

Primer lengths are well known to be an ordinary skill in the art. For example, in some embodiments, P1 or P2 or P3 is from 18 to 30 bases in length, e.g., 18, 19, 20, 21, 22, 23, 24, 25, 26, 27, 28, 29, 30 bases in length. The present invention is not limited to these primer lengths. In some embodiments, the primers may be less than 18 bases in length. In some embodiments the primers may be greater than 30 bases in length. For example, the primers may be from 30-40 bases in length, or more. Primers may be longer for various reasons such as but not limited to the user of an adapter.

In some embodiments, the sequence of the first nucleotide of P1 (e.g., the 5' end of P1) is from 18 to 25 bp upstream of the first nucleotide (5' end) of the target region. In some embodiments, the sequence of the first nucleotide of P1 (e.g., the 5' end of P1) is from 20 to 30 bp upstream of the first nucleotide (5' end) of the target region. In some embodiments, the sequence of the first nucleotide of P1 (e.g., the 5' end of P1) is from 30 to 40 bp upstream of the first nucleotide (5' end) of the target region. In some embodiments, the sequence of the first nucleotide of P1 (e.g., the 5' end of P1) is from 40 to 50 bp upstream of the first nucleotide (5' end) of the target region. In some embodiments, the sequence of the first nucleotide of P1 (e.g., the 5' end of P1) is from 50 to 60 bp upstream of the first nucleotide (5' end) of the target region. In some embodiments, the sequence of the first nucleotide of P1 (e.g., the 5' end of P1) is from 60 to 70 bp upstream of the first nucleotide (5' end) of the target region. In some embodiments, the sequence of the first nucleotide of P1 (e.g., the 5' end of P1) is from 70 to 80 bp upstream of the first nucleotide (5' end) of the target region. In some embodiments, the sequence of the first nucleotide of P1 (e.g., the 5' end of P1) is from 80 to 100 bp upstream of the first nucleotide (5' end) of the target region.

In some embodiments, the sequence of the first nucleotide of P1 (e.g., the 5' end of P1) is from 100 to 200 bp upstream of the first nucleotide (5' end) of the target region. In some embodiments, the sequence of the first nucleotide of P1 (e.g., the 5' end of P1) is more than 200 bp upstream of the first nucleotide (5' end) of the target region. The present invention is not limited to the aforementioned positional relationships.

In some embodiments, the sequence of the first nucleotide of P3 (e.g., the 5' end of P3) is from 0 to 5 bp upstream of the first nucleotide (5' end) of the complement of the target region. In some embodiments, the sequence of the first nucleotide of P3 (e.g., the 5' end of P3) is from 5 to 15 bp upstream of the first nucleotide (5' end) of the complement of the target region. In some embodiments, the sequence of the first nucleotide of P3 (e.g., the 5' end of P3) is from 15 to 25 bp upstream of the first nucleotide (5' end) of the complement of the target region. In some embodiments, the sequence of the first nucleotide of P3 (e.g., the 5' end of P3) is from 25 to 50 bp upstream of the first nucleotide (5' end) of the complement of the target region. In some embodiments, the sequence of the first nucleotide of P3 (e.g., the 5' end of P3) is from 50 to 75 bp upstream of the first nucleotide (5' end) of the complement of the target region. In some embodiments, the sequence of the first nucleotide of P3 (e.g., the 5' end of P3) is from 75 to 100 bp upstream of the first nucleotide (5' end) of the complement of the target region. In some embodiments, the sequence of the first nucleotide of P3 (e.g., the 5' end of P3) is more than 100 bp upstream of the first nucleotide (5' end) of the complement of the target region. The present invention is not limited to the aforementioned positional relationships.

The present invention features a method of real time asymmetric semi-nested isothermal nucleotide amplification (ANINA) for producing and quantifying single-stranded oligonucleotide amplicons. In some embodiments, the method comprises introducing to a sample a set of primers. In some embodiments, the set of primers comprise a first forward primer (FP1), a second forward primer (FP2), and a reverse primer (RP). In some embodiments, the FP2 is downstream of FP1. In some embodiments, the ratio of P1:P2:P3 (e.g., FP1:FP2:RP) is (1-10):(10-200):(1-10). In other embodiments, the ratio of P1:P2:P3 (e.g., FP1:FP2:RP) is 1:(20-200):(2-10). In further embodiments, the ratio of FP1:FP2:RP is 1:(50-100):3. In some embodiments, the method comprises introducing to a sample a solution comprising one or more enzymes, dNTPs, one or more buffering reagents, one or more salts, and one or more crowding reagents and a reporter probe. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the RP and a sequence extending from and including at least a portion of the FP2. In some embodiments, the method quantifies the single-stranded oligonucleotide amplicons produced when the single-stranded oligonucleotide amplicons bind to the reported probe.

The present invention may also feature a method of real time asymmetric semi-nested isothermal nucleotide amplification (ANINA) for producing and quantifying single-stranded oligonucleotide amplicons. In some embodiments, the method comprises introducing to a sample a set of primers. In some embodiments, the set of primers comprise a reverse primer (RP1), a second reverse primer (RP2) and a forward primer (FP). In some embodiments, the RP2 is upstream of RP1. In some embodiments, the ratio of RP1:RP2:FP is (1-10):(10-200):(1-10). In other embodiments, the ratio of RP1:RP2:FP1 is 1:(20-200):(2-10). In further embodiments, the ratio of RP1:RP2:FP is 1:(50-100):3. In some embodiments, the method comprises introducing to a sample a solution comprising one or more enzymes, dNTPs, one or more buffering reagents, one or more salts, and one or more crowding reagents and a reporter probe. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the FP and a sequence extending from and including at least a portion of the RP2. In some embodiments, the method quantifies the single-stranded oligonucleotide amplicons produced when the single-stranded oligonucleotide amplicons bind to the reported probe.

In some embodiments, the reporter probe is a fluorescent probe. In other embodiments, the reporter probe is a redox probe.

The present invention features a method of asymmetric semi-nested isothermal nucleotide amplification (ANINA) for producing single-stranded oligonucleotide amplicons. In some embodiments, said method comprises introducing to a sample 1) a set of primers comprising a first forward primer (FP1), a second forward primer (FP2), and a reverse primer (RP). In some embodiments. FP2 is downstream of FP1 In some embodiments, the ratio of FP1:FP2:RP is (1-10):(10-200):(1-10). In other embodiments, the ratio of FP1:FP2:RP is 1:(20-200):(2-10). In further embodiments, the ratio of FP1:FP2:RP is 1:(50-100):3. In some embodiments, the method comprises introducing to a sample 2) a solution comprising enzymes. ATP, dNTPs, and a buffer comprising buffering agents, salts, crowding reagents, and reducing reagents. In other embodiments, the method comprises introducing to a sample 2) a solution comprising enzymes, dATP, dNTPs, and a buffering agent comprising salts, crowding reagents, and reducing reagents. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the RP and a sequence extending from and including at least a portion of the FP2.

The present invention features a method of asymmetric semi-nested isothermal nucleotide amplification (ANINA) for producing single-stranded oligonucleotide amplicons. In some embodiments, said method comprises introducing to a sample 1) a set of primers comprising a first reverse primer (RP1), a second reverse primer (RP2), and a forward primer (FP). In some embodiments, RP2 is upstream of RP1. In some embodiments, the ratio of RP1:RP2:FP is (1-10):(10-200):(1-10). In other embodiments, the ratio of RP1:RP2: FP1 is 1:(20-200):(2-10). In further embodiments, the ratio of RP1:RP2:FP is 1:(50-100):3. In some embodiments, the method comprises introducing to a sample 2) a solution comprising enzymes, dNTPs, and a buffer comprising buffering agents, salts, and crowding reagents. In other embodiments, the method comprises introducing to a sample 2) a solution comprising enzymes, dATP, dNTPs. and a buffering agent comprising salts, crowding reagents, and reducing reagents. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the FP and a sequence extending from and including at least a portion of the RP2.

In some embodiments, the enzymes comprise a recombinase enzyme, a single strand binding protein, and a strand displacing polymerase. In some embodiments, the recombinase enzyme is an *Escherichia coli* (*E. coli*) RecA. In other embodiments, the recombinase enzyme is a homologous protein of RecA including but not limited to Rad51 in eukaryotes, and RadA in archaea. In accordance with the methods described herein other recombinase enzymes may be used. e.g., recombinase enzymes in the RecA/Rad51 family of enzymes. In some embodiments, the single-stranded binding protein is *Escherichia coli* single-stranded DNA binding protein (EcSSB). In other embodiments, the single-stranded binding protein is a single-stranded binding protein from a virus; non-limiting examples include but are not limited to a GP32 protein from T4 phage, or an ICP8 protein from HSV-1. In some embodiments, the single-stranded binding protein is eukaryotic mitochondrial single-stranded binding protein (mtSSB). In accordance with the methods described herein other single-stranded binding proteins may be used. In some embodiments, the strand displacing polymerase is *Bacillus subtilis* DNA polymerase I (Bsu). In other embodiments, the strand displacing polymerase is *Bacillus stearothermophilus* DNA Polymerase I (Bst). In further embodiments, the strand displacing polymerase is a Klenow Fragment. Non-limiting examples of strand displacing polymerases include but are not limited to phi29, T4 DNA polymerase and other mesophilic and psychrophilic DNA/RNA polymerases.

In some embodiments, the buffer may comprise buffering agents. As used herein a "buffering agent" refers to a weak acid or base solution used to maintain the acidity (pH) of a solution near a chosen value. Non-limiting examples of buffering agents that may be used in the buffer may include but are not limited to Tris, Tris-HCl, Tris Acetate. PBS, or a combination thereof.

In some embodiments, the buffer may comprise salts. Non-limiting examples of salt that may be used in the buffer may include but are not limited to sodium chloride (NaCl), potassium chloride (KCl), magnesium chloride ($MgCl_2$), sodium acetate ($NaCH_2COO$), magnesium acetate (Mg $(CH_2H_2O_2)_2$, monosodium phosphate (NaH2PO4), disodium phosphate ($NA_2PO_4$), or a combination thereof.

In some embodiments, the buffer may comprise a reducing agent. As used herein, a "reducing agent" refers to a substance that tends to bring about a reduction reaction by being oxidized and losing electrons. Non-limiting examples of reducing agents that may be used in the buffer may include but are not limited to dithiothreitol (OTT), tris(2-carboxyethyl)phosphine (TCEP), or a combination thereof.

In some embodiments, the buffer may comprise a crowding agent. As used herein, a "crowding agent" refers to inert, non-charged polymers of certain sizes, that occupy space but do not interact with target proteins. Non-limiting examples of crowding agents that may be used in the buffer may include but are not limited to polyvinylpyrrolidone (PVP), or polyethylene glycol (PEG), Ficoll. Dextran, or a combination thereof.

In some embodiments, the methods described herein amplify the oligonucleotide amplicons at an exponential rate. In some embodiments, the methods described herein amplify a single-stranded oligonucleotide amplicon of interest. In other embodiments, the methods described herein amplify a single-stranded target sequence. In some embodiments, at least 60% of the oligonucleotide amplicons are single-stranded. In other embodiments, at least 65% of the oligonucleotide amplicons are single-stranded. In some embodiments, at least 70% of the oligonucleotide amplicons are single-stranded. In other embodiments, at least 75% of the oligonucleotide amplicons are single-stranded. In some embodiments, at least 80% of the oligonucleotide amplicons are single-stranded. In other embodiments, at least 85% of the oligonucleotide amplicons are single-stranded. In some embodiments, at least 90% of the oligonucleotide amplicons are single-stranded. In other embodiments, at least 95% of the oligonucleotide amplicons are single-stranded. In some embodiments, at least 100% of the oligonucleotide amplicons are single-stranded.

In some embodiments, the oligonucleotide amplicons comprise DNA, RNA, synthetic oligonucleotides, or a combination thereof. In some embodiments, the methods described herein may further comprise a reverse transcriptase enzyme to produce complementary DNA (cDNA) from RNA oligonucleotide amplicons.

In some embodiments, the methods described herein do not require thermal melting of double-stranded oligonucleotides. In some embodiments, the reaction temperature may range from about 10° C. to 75° C. In some embodiments, the reaction temperature may range from about 10° C. to 80° C. in some embodiments, the reaction temperature may range from about 10° C. to 45° C. In some embodiments, the reaction temperature may range from about 101° C. to 30° C. in some embodiments, the reaction temperature may range from about 10° C. to 15° C. In some embodiments, the reaction temperature may range from about 15° C. to 75° C. In some embodiments, the reaction temperature may range from about 15° C. to 60° C. In some embodiments, the reaction temperature may range from about 15° C. to 45° C. In some embodiments, the reaction temperature may range from about 15° C. to 30° C.

In some embodiments, the reaction temperature is 15° C. In other embodiments, the reaction temperature is 20° C. In some embodiments, the reaction temperature is 25° C. In some embodiments, the reaction temperature is 30° C. In other embodiments, the reaction temperature is 35° C. In other embodiments, the reaction temperature is 37° C. In some embodiments, the reaction temperature is 40° C.

In some embodiments, the reaction temperature is 45° C. In some embodiments, the reaction temperature is 50° C. In some embodiments, the reaction temperature is 55° C. In some embodiments, the reaction temperature is 60° C.

In some embodiments, the length of time of the reaction may range from about 5 minutes to 60 minutes. In some embodiments, the length of time of the reaction may range from about 5 minutes to 45 minutes. In some embodiments, the length of time of the reaction may range from about 5 minutes to 30 minutes. In some embodiments, the length of time of the reaction may range from about 5 minutes to 20 minutes. In some embodiments, the length of time of the reaction may range from about 5 minutes to 15 minutes. In some embodiments, the length of time of the reaction may range from about 10 minutes to 60 minutes. In some embodiments, the length of time of the reaction may range from about 10 minutes to 45 minutes. In some embodiments, the length of time of the reaction may range from about 10 minutes to 30 minutes. In some embodiments, the length of time of the reaction may range from about 10 minutes to 15 minutes. In some embodiments, the length of time of the reaction may range from about 20 minutes to 60 minutes. In some embodiments, the length of time of the reaction may range from about 20 minutes to 45 minutes. In some embodiments, the length of time of the reaction may range from about 20 minutes to 30 minutes. In some embodiments, the length of time of the reaction may range from about 30 minutes to 60 minutes. In some embodiments, the length of time of the reaction may range from about 30 minutes to 45 minutes. In some embodiments, the length of time of the reaction is 30 minutes.

In preferred embodiments, the pH of the buffer ranges from a pH of 7.4 to a pH of 7.7. In some embodiments, the pH of the buffer ranges from a pH of 6.5 to a pH of 8.5. In some embodiments, the pH of the buffer ranges from a pH of 6.5 to a pH of 8.0. In some embodiments, the pH of the buffer ranges from a pH of 6.5 to a pH of 7.5. In some embodiments, the pH of the buffer ranges from a pH of 6.5 to a pH of 7.0 In some embodiments, the pH of the buffer ranges from a pH of 7.0 to a pH of 8.5. In some embodiments, the pH of the buffer ranges from a pH of 7.0 to a pH of 8.0. In some embodiments, the pH of the buffer ranges from a pH of 7.0 to a pH of 7.7. In some embodiments, the pH of the buffer ranges from a pH of 7.0 to a pH of 7.5. In some embodiments, the pH of the buffer ranges from a pH of 7.0 to a pH of 7.4. In some embodiments, the pH of the buffer ranges from a pH of 7.4 to a pH of 8.5. In some embodiments, the pH of the buffer ranges from a pH of 7.4 to a pH of 8.0. In some embodiments, the pH of the buffer ranges from a pH of 7.5 to a pH of 8.5. In some embodiments, the pH of the buffer ranges from a pH of 7.5 to a pH of 8.0. In some embodiments, the pH of the buffer ranges from a pH of 7.5 to a pH of 7.7.

The present invention features a method of point-of-care amplification of a target sequence. In some embodiments, said method comprises introducing to a sample 1) a set of primers comprising a first forward primer (FP1), a second forward primer (FP2), and a reverse primer (RP). In some embodiments, FP2 is downstream of FP1. In some embodiments, the ratio of FP1:FP2:RP is (1-10):(10-200):(1-10). In other embodiments, the ratio of FP1:FP2:RP is 1:(20-200): (2-10). In further embodiments, the ratio of FP1:FP2:RP is 1:(50-100):3. In some embodiments, said method comprises introducing to a sample 2) a solution comprising enzymes, dNTPs, and a buffer comprising a buffering agent, salts, and crowding reagents. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the RP and a sequence extending from and including at least a portion of the FP2.

In other embodiments, the present invention features a method of point-of-care amplification of a target sequence. In some embodiments, said method comprises introducing to a sample 1) a set of primers comprising a first reverse primer (RP1), a second reverse primer (RP2), and a forward primer (FP). In some embodiments. RP2 is upstream of RP1. In some embodiments, the ratio of RP1:RP2:FP is (1-10): (10-200):(1-10). In other embodiments, the ratio of RP1: RP2:FP1 is 1:(20-200):(2-10). In further embodiments, the ratio of RP1:RP2:FP is 1:(50-100):3. In some embodiments, said method comprises introducing to a sample 2) a solution comprising enzymes, dNTPs, and a buffer comprising a buffer agent, salts, and crowding reagents. In some embodiments, the method comprises incubating the sample with the primers and solution at a reaction temperature for a length of time. In some embodiments, the method produces single-stranded oligonucleotide amplicons according to a sequence comprising at least a portion of a complementary sequence of the FP and a sequence extending from and including at least a portion of the RP2.

In some embodiments, the point-of-care method described herein is performed at the site where the sample is obtained. In some embodiments, the method further comprises incubating the sample with the primers and solution in a reaction chamber. In some embodiments, the reaction chamber is a thermal cycler (or polymerase chain reaction (PCR) machine). In some embodiments, the reaction chamber is portable. In other embodiments, the method further comprises incubating the sample with the primers and solution in a closed system. In some embodiments, the closed system may include but is not limited to a microcentrifuge tube.

In some embodiments, Lateral flow strip (LFA) comprising test line for biotin probe and gold nanoparticles labeled with anti-FITC antibody may be used to detect ANINA amplicons and with FITC-FP using in reaction biotin probe, or vice versa. This method can easily be done in a point-of need setting.

In other embodiments, the method further comprises detecting the target sequence. In some embodiments, a "target sequence" refers to a single-stranded oligonucleotide amplicon according to a sequence including a complementary sequence of the RP and extending to and including the complementary sequence of FP2. In some embodiments, the detection of the target sequence comprises introducing a genosensor probe. In some embodiments, the target sequence is in the sense strand. In other embodiments, the target sequence is in the antisense strand. In some embodiments, the genosensor probe is complementary to the target sequence. In other embodiments, the genosensor probe hybridizes with the target sequence. In some embodiments, the genosensor probe is a single-stranded (ss) DNA probe. In other embodiments, the genosensor probe is an ssRNA probe. In further embodiments, the genosensor probe is a peptide nucleic acid (PNA) probe.

In some embodiments, the first forward primer (FP1) sequence is located on the same strand as the target sequence and is upstream (more 5') of the target sequence. In some embodiments, the second forward primer (FP2) sequence is located on the same strand as the target sequence and is downstream (more 3') of FP1 but is upstream of the target sequence (more 5') to the target sequence. In some embodiments, the reverse primer (RP) sequence is located on the complementary strand containing the target sequence and is downstream (more 3') to the complementary sequence of FP1, FP2, and the target sequence.

Figure 5:
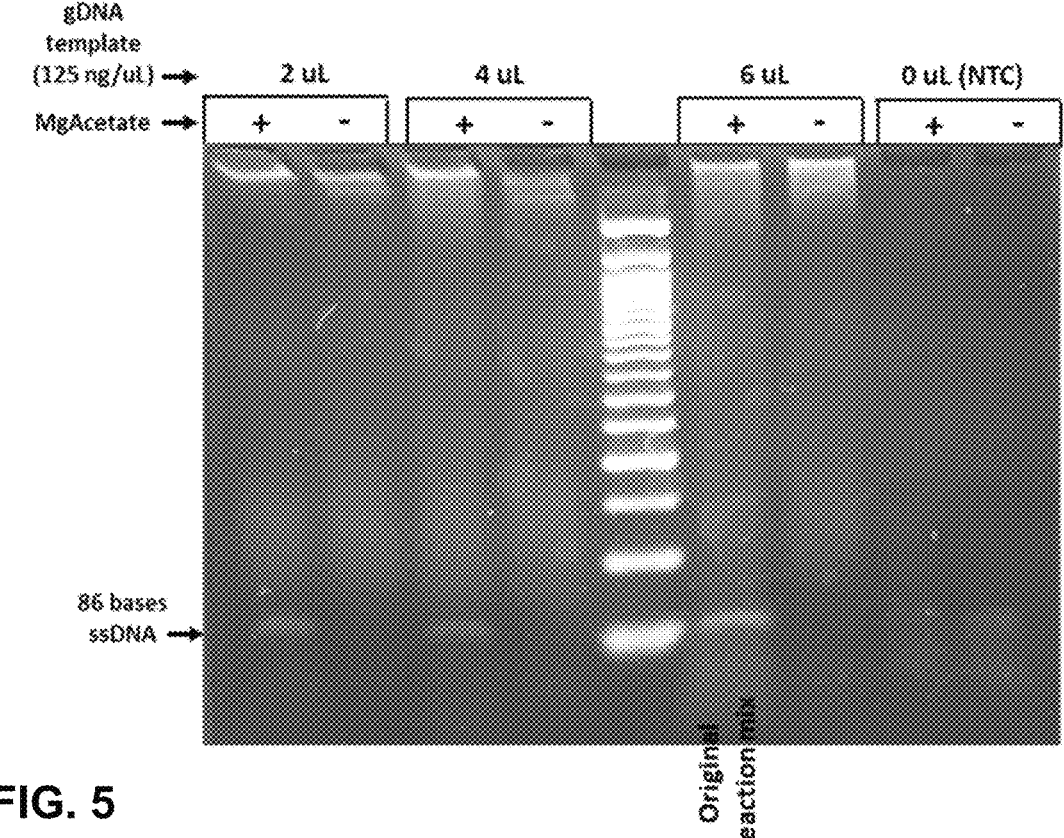
FIG. 5 shows the ANINA optimization using the required amount of Mg Acetate and increasing gDNA amount.
Figure 6:
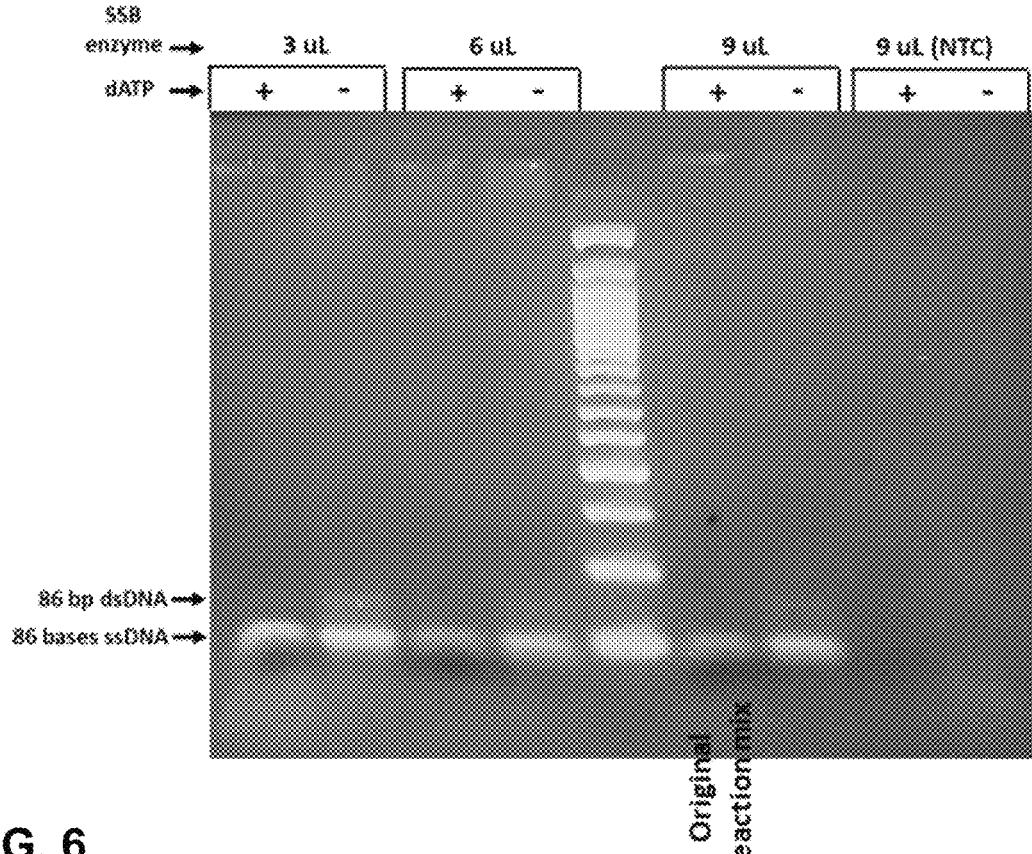
FIG. 6 shows the ANINA optimization in the presence and absence of dATP and different amounts of Single-Strand Binding (SSB) enzymes.
Figure 7:
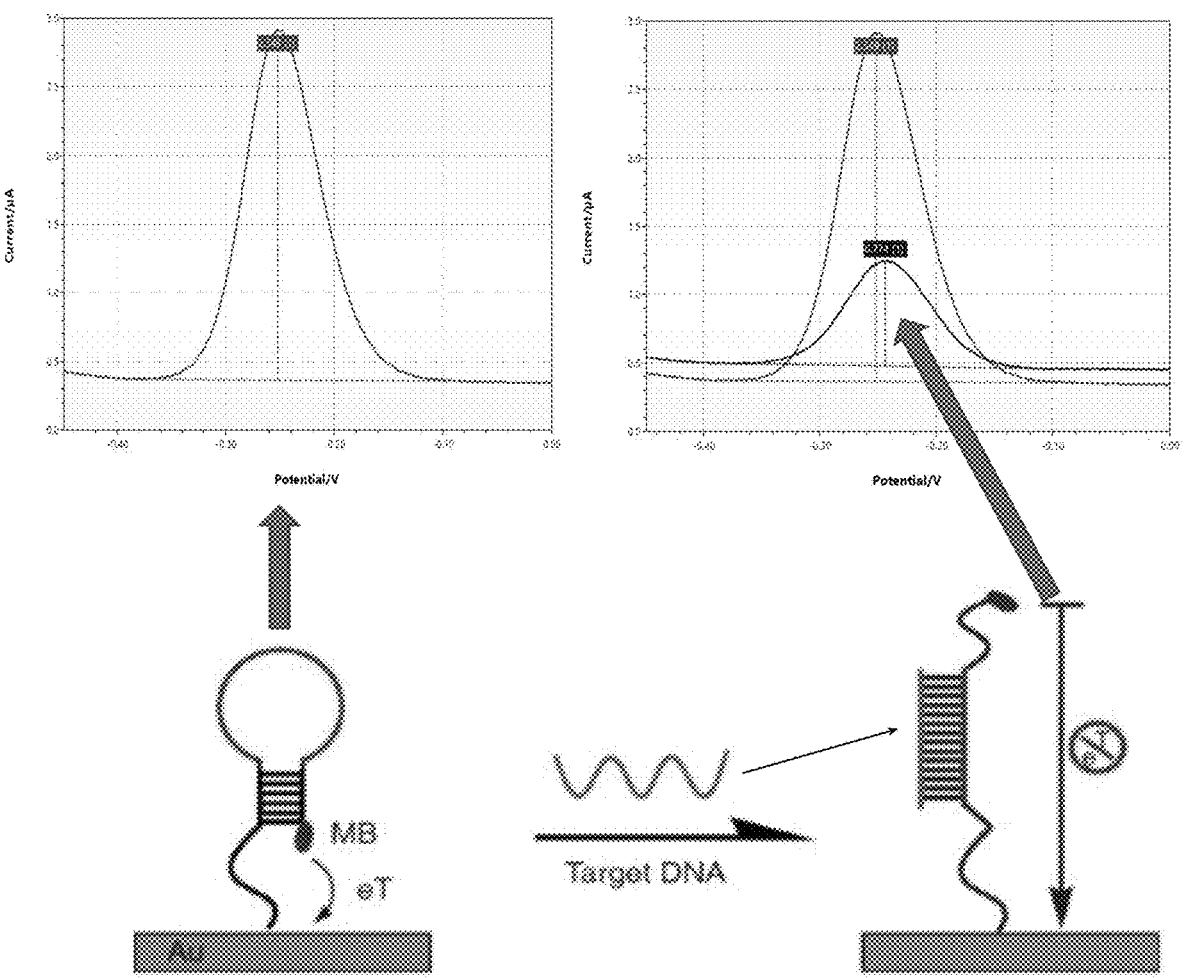
FIG. 7 shows a non-limiting example of a genosensor probe platform as described herein.

In some embodiments, the ssDNA/RNA/PNA act as a capture probe. As used herein, a capture probe comprises one end that is covalently bound to a sensitive redox reporter (e.g., Methylene Blue (MB)) and another end that is covalently bound to a gold (Au) or platinum (Pt) surface of a test strip via thiol chemistry. In some embodiments, the capture probe has a stable secondary structure which allows efficient electron transfer from MB to Au surface and gives a high electrical signal (FIG. 5). In some embodiments, hybridization of the capture probe with complementary the ssDNA/ssRNA target decreases the electron transfer, leading to a decreased signal from initial up to 90% (dependent on concentration). In some embodiments, the decrease in signal is measured by a software system (over time-can be real-time) and leads to detection of the target.

In some embodiments, any redox reporter may be used including but not limited to methylene blue, ferrocene, a fluorophore, or any other physico-chemical detector that can be attached to DNA or can bind to DNA.

In some embodiments, the present invention features a composition for amplifying single-stranded oligonucleotides. In some embodiments, said composition comprising: a first forward primer (FP1), a second forward primer (FP2), wherein FP2 is downstream from FP1, and a reverse primer RP in some embodiments, the ratio of FP1:FP2:RP is (1-10):(10-200):(1-10). In other embodiments, the ratio of FP1:FP2:RP is 1:(20-200):(2-10). In further embodiments, the ratio of FP1:FP2:RP is 1:(50-100):3.

In some embodiments, the composition may further comprise a buffer. In some embodiments, the buffer comprises buffering reagents, salts, crowding reagents, and reducing reagents. In other embodiments, the composition further comprises enzymes. ATP or dATP, and dNTPs. In some embodiments, the enzymes may comprise a recombinase, a single strand binding protein, a strand displacing polymerase, a reverse transcriptase or a combination thereof.

In other embodiments, the present invention features a composition for amplifying single-stranded oligonucleotides. In some embodiments, said composition comprising: a first reverse primer (FP1), a second reverse primer (FP2), wherein FP2 is upstream from FP1, and a forward primer (FP). In some embodiments, the ratio of RP1:RP2:FP is (1-10):(10-200):(1-10). In other embodiments, the ratio of RP1:RP2:FP1 is 1:(20-200):(2-10). In further embodiments, the ratio of RP1:RP2:FP is 1:(50-100):3. In some embodiments, the composition may further comprise a buffer. In some embodiments, the buffer comprises buffering reagents, salts, crowding reagents, and reducing reagents. In other embodiments, the composition further comprises enzymes, ATP or dATP, and dNTPs. In some embodiments, the enzymes may comprise a recombinase, a single strand binding protein, a strand displacing polymerase, a reverse transcriptase or a combination thereof.

In some embodiments, the present invention features a kit for amplifying single-stranded oligonucleotides. In some embodiments, said kit comprises: a recombinase, a single-stranded binding protein, strand displacing polymerase, dNTPs, and a buffer. In some embodiments, the kit further comprises a reverse transcriptase. In other embodiments, said kit comprises: a first forward primer (FP1), a second forward primer (FP2), wherein FP2 is downstream from FP1, and a reverse primer (RP). In some embodiments, the ratio of FP1:FP2:RP is (1-10):(10-200):(1-10). In other embodiments, the ratio of FP1:FP2:RP is 1:(20-200):(2-10). In further embodiments, the ratio of FP1:FP2:RP is 1:(50-100):3.

In other embodiments, the present invention features a kit for amplifying single-stranded oligonucleotides. In some embodiments, said kit comprises: a recombinase, a single-stranded binding protein, strand displacing polymerase, dNTPs, and a buffer. In some embodiments, the kit further comprises a reverse transcriptase. In other embodiments, said kit comprises: a first reverse primer (RP1), a second reverse primer (RP2), wherein RP2 is upstream from RP1, and a forward primer (FP). In some embodiments, the ratio of FP1:RP2:FP is (1-10):(10-200):(1-10). In other embodiments, the ratio of RP1:RP2:FP1 is 1:(20-200):(2.10). In further embodiments, the ratio of RP1:RP2:FP is 1:(50-100):3.

In some embodiments, the recombinase enzyme is RecA. In some embodiments, the single-stranded binding protein is *Escherichia coli* single-stranded DNA binding protein (EcSSB). In some embodiments, the strand displacing polymerase is *Bacillus subtilis* DNA polymerase I (Bsu). In other embodiments, the strand displacing polymerase is *Bacillus stearothermophilus* DNA Polymerase I (Bst). In further embodiments, the strand displacing polymerase is a Klenow Fragment.

In some embodiments, the buffer comprises buffering agents, salts, crowding reagents, reducing agents, or a combination thereof. In some embodiments, the buffering agent is Tris, PBS, or a combination thereof. In other embodiments, the salt is NaCl, KCl, MgCl$_2$, Mg(C$_2$H$_2$O$_2$)$_2$ or a combination thereof. In some embodiments, the crowding reagent comprises PEG, PVP, or a combination thereof. In some embodiments, the reducing reagent is DTT or TCEP.

Other amplification reaction enhancement strategies, such as chemicals for destabilizing or stabilizing nucleic acid structure, stabilizing enzyme structures, sacrificial proteins, can be added for improving the reaction.

The present invention features a system for performing asymmetric semi-nested isothermal nucleotide amplification (ANINA) for producing single-stranded oligonucleotide amplicons as described herein. In some embodiments, said system comprises: a kit for amplifying single-stranded oligonucleotides as described herein and a reaction chamber for accepting the kit and a sample. In some embodiments, the reaction chamber is configured to incubate the kit and sample at a reaction temperature for a length of time such that the asymmetric semi-nested isothermal nucleotide amplification (ANINA) system amplifies a single-stranded amplicon therein.

In some embodiment, the single-stranded amplicon binds to a probe (e.g., an oligonucleotide comprising an indicator attached to a 5' end of the oligonucleotide, said 3' end of the oligonucleotide is attached to a gold surface (e.g., a surface of an electrochemical sensor). In some embodiments, the addition of a probe with a blocker at the 3' end will ensure a real time detection as the Bsu polymerase doesn't have 5'-3' or 3'-5 exonuclease so it cannot extend it and the ssDNA will bind to the probes in real time. In some embodiments, the probe produces a fluorescent, colormetric, electrochemical or chemical signal upon binding to the single-stranded amplicon (e.g., a target oligonucleotide).

Additional details about methods used to detect single-stranded amplicons (e.g., a target oligonucleotides) can be found in U.S. Application Ser. No. 17/715,868, the specification of which is hereby incorporated in its entirety by reference.

EMBODIMENTS

The following embodiments are intended to be illustrative only and not to be limiting in any way.

Embodiment Set A

Embodiment 1A: A method of asymmetric semi-nested isothermal nucleotide amplification for producing single-stranded oligonucleotide amplicons of a target region of nucleic acid, said method comprising: (a) introducing to a sample: (i) a set of primers comprising: a first primer (P1), P1 has a sequence that is a set of nucleotides 5' to the target region, wherein P1 binds to a first complementary binding region (CSBR1) which is on a strand opposite the target region: a second primer (P2), P2 has a sequence that is a set of nucleotides (a) 5' to the target region or (b) 5' to the target region and including a portion of the target region, wherein P2 binds to a second complementary binding region (CSBR2) which is on a strand opposite the target region: wherein the set of nucleotides for P1 is at least partially 5' to the set of nucleotides for P2; and a third primer (P3), P3 has a sequence that is a set of nucleotides complementary to (a) at least a portion of the target region, or (b) a portion of the 3' end of the target region and one or more nucleotides downstream of the 3' end of the target region; or (c) an area 3' to the target region; wherein P3 binds to a target strand binding region (TSBR) of the target strand; wherein the ratio of P1:P2:P3 is (1-10):(20-200):(1-20); and (ii) a solution comprising enzymes, dNTPs, and a buffer comprising buffering reagents, salts, and crowding reagents; and (b) incubating the sample with the primers and solution at a reaction temperature for a length of time; wherein the method produces single-stranded oligonucleotide amplicons having a sequence comprising at least the target region.

Embodiment 2A: The method of embodiment 1A, wherein the ratio of P1:P2:P3 is 1:(50-100):3.

Embodiment 3A: The method of embodiment 1A, wherein the target region is from 20 to 500 bases in length.

Embodiment 4A: The method of embodiment 1A or embodiment 2A, wherein the first primer is a first forward primer (FP1), the second primer is a second forward primer (FP2), and the third primer is a reverse primer (RP).

Embodiment 5A: The method of embodiment 1A or embodiment 2A, wherein the first primer is a first reverse primer (RP1), the second primer is a second reverse primer (RP2), and the third primer is a forward primer (FP).

Embodiment 6A: The method of any one of embodiments 1A-5A, wherein the buffer further comprises a reducing agent.

Embodiment 7A: The method of embodiment 6A, wherein the reducing agent is dithiothreitol (DTT), tris(2-carboxyethyl)phosphine (TCEP), or a combination thereof.

Embodiment 8A: The method of any one of embodiments 1A-7A, wherein the enzymes comprise a recombinase enzyme, a single strand binding protein, a strand displacing polymerase, a reverse transcriptase or a combination thereof.

Embodiment 9A: The method of embodiment 8A, wherein the recombinase is RecA, or Rad51, or RadA.

Embodiment 10A: The method of embodiment 8A, wherein the single-stranded binding protein is *Escherichia coli* single-stranded DNA binding protein (EcSSB).

Embodiment 11A: The method of embodiment 8A, wherein the strand displacing polymerase is *Bacillus subtilis* DNA polymerase I (Bsu), or mesophilic DNA polymerase.

Embodiment 12A. The method of any one of embodiments 1A-11A, wherein the buffering reagents are Tris, PBS, or a combination thereof.

Embodiment 13A: The method of any one of embodiments 1A-11A, wherein salts comprise sodium chloride (NaCl), potassium chloride (KCl), magnesium chloride (MgCl$_2$), sodium acetate (NaCH$_2$COO), magnesium acetate (Mg(C$_2$H$_2$O$_2$)$_2$, monosodium phosphate (NaH2PO4), disodium phosphate (NA$_2$PO$_4$), or a combination thereof.

Embodiment 14A: The method of anyone of embodiments 1A-11A, wherein the crowding agent is polyvinylpyrrolidone (PVP), or polyethylene glycol (PEG), Ficoll. Dextran, or a combination thereof.

Embodiment 15A: The method of embodiment 1A, wherein the method amplifies amplicons at an exponential rate.

Embodiment 16A: The method of embodiment 1A, wherein at least 75% of the amplicons are single-stranded.

Embodiment 17A: The method of embodiment 1A, wherein at least 95% of the amplicons are single-stranded.

Embodiment 18A: The method of embodiment 1A, wherein the single-stranded oligonucleotides are from 20 to 200 bp in length.

Embodiment 19A: The method of embodiment 1A, wherein the single-stranded oligonucleotides are from 20 to 500 bp in length.

Embodiment 20A: The method of embodiment 1A, wherein the oligonucleotides comprise DNA. RNA, synthetic oligonucleotides, or a combination thereof.

Embodiment 21A: The method of embodiment 1A, wherein the method does not require thermal melting of double-stranded oligonucleotides.

Embodiment 22A: The method of embodiment 1A, wherein the reaction temperature ranges from 15° C. to 60° C.

Embodiment 23A: The method of embodiment 22A, wherein the reaction temperature is 37° C.

Embodiment 24A: The method of embodiment 1, wherein the length of time is from 5 to 60 minutes.

Embodiment 25A: The method of embodiment 24, wherein the length of time is 30 minutes.

Embodiment 26A: The method of embodiment 1A, wherein the buffer has a pH ranging from 7.0-8.0.

Embodiment 27A: The method of embodiment 1A, wherein the buffer has a pH ranging from 7.0-8.0.

Embodiment 28A: The method any one of embodiments 1A-27A, wherein the method further comprises introducing a reporter probe to the sample.

Embodiment 29A: The method of embodiment 28A, wherein the method quantifies the single-stranded oligonucleotide amplicons produced when the single-stranded oligonucleotide amplicons bind to the reported probe.

Embodiment 30A: The method of embodiment 28A or embodiment 29A, wherein the reporter probe is a fluorescent probe.

Embodiment 31A: The method of embodiment 28A or embodiment 29A, wherein the reporter probe is a redox reporter.

Embodiment 32A: A method of asymmetric semi-nested isothermal nucleotide amplification for producing single-stranded oligonucleotide amplicons of a target region of nucleic acid, said method comprising: (a) introducing to a sample: (i) a set of primers comprising: a first primer (P1), P1 has a sequence that is a set of nucleotides 5' to the target region, wherein P1 binds to a first complementary binding region (CSBR1) which is on a strand opposite the target region; a second primer (P2), P2 has a sequence that is a set of nucleotides (a) 5' to the target region or (b) 5' to the target region and including a portion of the target region, wherein P2 binds to a second complementary binding region (CSBR2) which is on a strand opposite the target region; wherein the set of nucleotides for P1 is at least partially 5' to the set of nucleotides for P2; and a third primer (P3). P3 has a sequence that is a set of nucleotides complementary to (a) at least a portion of the target region, or (b) a portion of the 3' end of the target region and one or more nucleotides downstream of the 3' end of the target region: or (c) an area 3' to the target region; wherein P3 binds to a target strand binding region (TSBR) of the target strand; wherein the ratio of P1:P2:P3 is (1-10):(20-200):(1-20); (ii) a solution comprising enzymes, dNTPs, and a buffer comprising buffering reagents, salts, and crowding reagents, (iii) and a reporter probe; and (b) incubating the sample with the primers and solution at a reaction temperature for a length of time; wherein the method produces single-stranded oligonucleotide amplicons having a sequence comprising at least the target region; wherein the method quantifies the single-stranded oligonucleotide amplicons produced when the single-stranded oligonucleotide amplicons bind to the reported probe.

Embodiment Set B

Embodiment 18: A method of asymmetric semi-nested isothermal nucleotide amplification for producing single-stranded oligonucleotide amplicons of a target region, said method comprising: (a) introducing to a sample: (i) a set of primers comprising a first forward primer (FP1), a second forward primer (FP2), and a reverse primer (RP), wherein FP2 is downstream of FP1; wherein the ratio of FP1:FP2:RP is (1-10)-(20-200):(1-20); (ii) a solution comprising enzymes, dNTPs, and a buffer comprising buffering reagents, salts, and crowding reagents; and (b) incubating the sample with the primers and solution at a reaction temperature for a length of time; wherein the method produces single-stranded oligonucleotide amplicons according to a sequence comprising at least a portion of a complementary sequence of the RP and a sequence extending from and including at least a portion of the FP2.

Embodiment 2B: The method of embodiment 1B, wherein the ratio of FP1:FP2:RP is 1:(50-100):3.

Embodiment 38: A method of asymmetric semi-nested isothermal nucleotide amplification for producing single-stranded oligonucleotide amplicons of a target region, said method comprising: (a) introducing to a sample: (i) a set of primers comprising a first reverse primer (RP1), a second reverse primer (RP2) and a forward primer (FP), wherein RP2 is upstream of RP1; wherein the ratio of RP1:RP2:FP1 is (1-10):(20-200):(1-20); (ii) a solution comprising enzymes, dNTPs, and a buffer comprising buffering reagents, salts, and crowding reagents; and (b) incubating the sample with the primers and solution at a reaction temperature for a length of time; wherein the method produces single-stranded oligonucleotide amplicons according to a sequence comprising at least a portion of a complementary sequence of the FP and a sequence extending from and including at least a portion of the RP2.

Embodiment 48. The method of embodiment 3B, wherein the ratio of RP1:RP2:FP is 1:(50-100):3.

Embodiment 5B: The method of any one of embodiments 1B-4B, wherein the buffer further comprises a reducing agent.

Embodiment 5B: The method of embodiment 5B, wherein the reducing agent is dithiothreitol (DTT), tris(2-carboxyethyl)phosphine (TCEP), or a combination thereof.

Embodiment 7B: The method of any one of embodiments 1B-6B, wherein the enzymes comprise a recombinase enzyme, a single strand binding protein, a strand displacing polymerase, a reverse transcriptase or a combination thereof.

Embodiment 8B: The method of embodiment 7B, wherein the recombinase is RecA, or Rad51, or RadA.

Embodiment 9B: The method of embodiment 7B, wherein the single-stranded binding protein is *Escherichia coli* single-stranded DNA binding protein (EcSSB).

Embodiment 10B: The method of embodiment 7B, wherein the strand displacing polymerase is *Bacillus subtilis* DNA polymerase I (Bsu), or mesophilic DNA polymerase.

Embodiment 11B: The method of any one of embodiments 1B-10B, wherein the buffering reagents are Tris, PBS, or a combination thereof.

Embodiment 12B: The method of any one of embodiments 1B-10B, wherein salts comprise sodium chloride (NaCl), potassium chloride (KCl), magnesium chloride (MgCl$_2$), sodium acetate (NaCH$_2$COO), magnesium acetate (Mg(C$_2$H$_2$O$_2$)$_2$, monosodium phosphate (NaH2PO4), disodium phosphate (NA$_2$PO$_4$), or a combination thereof.

Embodiment 13B: The method of any one of embodiments 1B-10B, wherein the crowding agent is polyvinylpyrrolidone (PVP), or polyethylene glycol (PEG), Ficoll, Dextran, or a combination thereof.

Embodiment 14B: The method of embodiment 1B or embodiment 3B, wherein the method amplifies amplicons at an exponential rate.

Embodiment 15B: The method of embodiment 1B or embodiment 3B, wherein at least 60% of the amplicons are single-stranded.

Embodiment 16B: The method of embodiment 1B or embodiment 3B, wherein at least 75% of the amplicons are single-stranded.

Embodiment 17B: The method of embodiment 1B or embodiment 3B, wherein at least 90% of the amplicons are single-stranded.

Embodiment 18B: The method of embodiment 1B or embodiment 3B, wherein at least 95% of the amplicons are single-stranded.

Embodiment 19B: The method of embodiment 1B or embodiment 3B, wherein at least 100% of the amplicons are single-stranded.

Embodiment 20B: The method of embodiment 1B or embodiment 3B, wherein the single-stranded oligonucleotides are from 25 to 100 bp in length.

Embodiment 21B: The method of embodiment 1B or embodiment 3B, wherein the single-stranded oligonucleotides are from 20 to 200 bp in length.

Embodiment 22B: The method of embodiment 1B or embodiment 3B, wherein the single-stranded oligonucleotides are from 20 to 500 bp in length.

Embodiment 23B: The method of embodiment 1B or embodiment 3B, wherein the oligonucleotides comprise DNA, RNA, synthetic oligonucleotides, or a combination thereof.

Embodiment 24B: The method of embodiment 1B or embodiment 3B, wherein the method does not require thermal melting of double-stranded oligonucleotides.

Embodiment 25B: The method of embodiment 1B or embodiment 3B, wherein the reaction temperature ranges from 15° C. to 60° C.

Embodiment 26B: The method of embodiment 25B, wherein the reaction temperature is 37° C.

Embodiment 27B: The method of embodiment 1B or embodiment 3B, wherein the length of time is 30 minutes.

Embodiment 28B: The method of embodiment 1B or embodiment 3B, wherein the length of time is from 5 to 60 minutes.

Embodiment 29B: The method of embodiment 1B or embodiment 3B, wherein the buffer has a pH ranging from 7.0-8.0.

Embodiment 30B: The method of embodiment 29B, wherein the buffer has a pH ranging 7.4-7.7

Embodiment 31B: The method any one of embodiments 1B-30B, wherein the method further comprises introducing a reporter probe to the sample.

Embodiment 32B: The method of embodiment 31B, wherein the method quantifies the single-stranded oligonucleotide amplicons produced when the single-stranded oligonucleotide amplicons bind to the reported probe.

Embodiment 33B: The method of embodiment 31B or embodiment 32B, wherein the reporter probe is a fluorescent probe.

Embodiment 34B: The method of embodiment 31B or embodiment 32B, wherein the reporter probe is a redox reporter.

Embodiment 35B: A method of point-of-care amplification of a single-stranded target oligonucleotide sequence, said method comprising: (a) introducing to a sample: (i) a set of primers comprising a first forward primer (FP1), a second forward primer (FP2), and a reverse primer (RP), wherein FP2 is downstream of FP1: wherein the ratio of FP1:FP2:RP is (1-10):(20-200):(1-20); and (ii) a solution comprising enzymes, dNTPs, and a buffer comprising buffering agent, salts, and crowding reagents, and (b) incubating the sample with the primers and solution at a reaction temperature for a length of time; wherein the method produces single-stranded oligonucleotide amplicons according to a sequence comprising at least a portion of a complementary sequence of the RP and a sequence extending from and including at least a portion of the FP2.

Embodiment 36B: The method of embodiment 34B, wherein the ratio of FP1:FP2:RP is 1:(50-100):3.

Embodiment 37B: A method of point-of-care amplification of a single-stranded target oligonucleotide sequence, said method comprising: (a) introducing to a sample: (i) a set of primers comprising a first forward primer (RP1), a second forward primer (RP2), and a reverse primer (FP), wherein RP2 is upstream of RP1; wherein the ratio of RP1:RP2:FP is (1-10):(20-200):(1-20); and (ii) a solution comprising enzymes, dNTPs. and a buffer comprising buffering agent, salts, and crowding reagents; and (b) incubating the sample with the primers and solution at a reaction temperature for a length of time; wherein the method produces single-stranded oligonucleotide amplicons according to a sequence comprising at least a portion of a complementary sequence of the FP and a sequence extending from and including at least a portion of the RP2.

Embodiment 38B: The method of embodiment 37B, wherein the ratio of RP1:RP2:FP is 1:(50-100):3.

Embodiment 39B: The method of any one of embodiments 35B-38B, wherein the method is performed at the site where the sample is obtained.

Embodiment 40B: The method of any one of embodiments 35B-39B, wherein the method further comprises incubating the sample with the primers and solution in a reaction chamber.

Embodiment 41B: The method of embodiment 40B, wherein the reaction chamber is portable.

Embodiment 42B: The method of any one of embodiments 35B-41B, wherein the method further comprises detecting the target sequence.

Embodiment 43B: The method of embodiment 42B, wherein detection of the target sequence comprises introducing a genosensor probe.

Embodiment 44B: The method of embodiment 43B, wherein the genosensor probe is a single-strand DNA, RNA, or PNA molecule.

Embodiment 45B: The method of embodiment 44B, wherein the genosensor probe is complementary to the single-stranded target oligonucleotide sequence.

Embodiment 46B: The method of embodiment 45B, wherein the genosensor probe hybridizes with the single-stranded target oligonucleotide sequence.

Embodiment 478: A composition for amplifying single-stranded oligonucleotides, said composition comprising: (a) a first forward primer (FP1); (b) a second forward primer (FP2), wherein (FP2) is downstream from (FP1); and (c) a reverse primer (RP); wherein the ratio of FP1:FP2:RP is (1-10):(20-200):(1-20).

Embodiment 48B: The composition of embodiment 47B, wherein the ratio of FP1:FP2:RP is 1:(50-100):3.

Embodiment 49B: A composition for amplifying single-stranded oligonucleotides, said composition comprising: (a) a first reverse primer (RP1); (b) a second reverse primer (RP2), wherein (RP2) is upstream from (RP1); and (c) a reverse primer (FP); wherein the ratio of RP1:RP2:FP is (1-10):(20-200):(1-20).

Embodiment 50B: The composition of embodiment 49B, wherein the ratio of RP1:RP2:FP is 1:(50-100):3.

Embodiment 51B: The composition of any one of embodiments 47B-50B further comprising a buffer Embodiment 52B: The composition of embodiment 51B, wherein the buffer comprises a buffer comprising buffering reagents, salts, crowding reagents, and reducing agents.

Embodiment 53B: The composition of any one of embodiments 47B-52B further comprising a recombinase, a single strand binding protein, a strand displacing polymerase, a reverse transcriptase, or a combination thereof.

Embodiment 54B: A kit for amplifying single-stranded oligonucleotides, said kit comprising: (a) a recombinase: (b) a single-stranded binding protein; (c) strand displacing polymerase: (d) dNTPs; (e) a buffer: (f) a first forward primer (FP1); (g) a second forward primer (FP2), wherein (FP2) is downstream from (FP1); and (h) a reverse primer (RP); wherein the ratio of FP1:FP2:RP is (1-10):(20-200):(1-20).

Embodiment 55B: The Kit of embodiment 50, wherein the ratio of FP1:FP2:RP is 1:(50-100):3.

Embodiment 56B: A kit for amplifying single-stranded oligonucleotides, said kit comprising: (a) a recombinase; (b) a single-stranded binding protein; (c) strand displacing polymerase; (d) dNTPs: (e) a buffer (f) a first reverse primer (RP1): (g) a second reverse primer (RP2), wherein RP2 is upstream from RP1; and (h) a forward primer (FP); wherein the ratio of FP1:FP2:RP is (1-10):(20-200):(1-20).

Embodiment 57B: The kit of embodiment 56B, wherein the ratio of RP1:RP2:FP is 1:(50-100):3.

Embodiment 58B: The kit of any one of embodiments 558-578, further comprising a reverse transcriptase.

Embodiment 59B: The kit of any of embodiments 54B-58B, wherein the recombinase is RecA.

Embodiment 60B: The kit of any of embodiments 54B-59B, wherein the single-stranded binding protein is *Escherichia coli* single-stranded DNA binding protein (EcSSB).

Embodiment 61B: The kit of any of embodiments 54B-59B, wherein the single-stranded binding protein is *Escherichia coli* single-stranded DNA binding protein (EcSSB).

Embodiment 62B: The kit of embodiment 54B or embodiment 56B, wherein the buffer comprises buffering reagents, salts, crowding reagents, reducing reagents, or a combination thereof.

Embodiment 63B: The kit of embodiment 62B, wherein the buffering reagents are Tris, PBS, or a combination thereof.

Embodiment 64B: The kit of embodiment 62B, wherein salts comprise sodium chloride (NaCl), potassium chloride (KCl), magnesium chloride ($MgCl_2$), sodium acetate ($NaCH_2COO$), magnesium acetate ($Mg(C_2H_2O_2)_2$, monosodium phosphate (NaH2PO4), disodium phosphate ($NA_2PO_4$), or a combination thereof.

Embodiment 65B: The kit of embodiment 62B, wherein the reducing agent is dithiothreitol (DTT), tris(2-carboxyethyl)phosphine (TCEP), or a combination thereof.

Embodiment 66B: The kit of embodiment 62B, wherein the crowding agent is polyvinylpyrrolidone (PVP), or polyethylene glycol (PEG), Ficoll, Dextran, or a combination thereof.

Embodiment 67B: A system for performing asymmetric semi-nested nucleotide amplification for producing single-stranded oligonucleotide amplicons according to any one of embodiments 1B-34B, said system comprising: (a) a kit according to any one of embodiments 54B-66B; and (b) a reaction chamber for accepting the kit, the set of primers, and a sample: the reaction chamber is configured to incubate the kit, set of primers, and sample at a reaction temperature for a length of time such that asymmetric semi-nested nucleotide amplification system amplifies a single-stranded amplicon therein.

Embodiment Set C

Embodiment 1C: A method of real time asymmetric semi-nested isothermal nucleotide amplification (ANINA) for producing and quantifying single-stranded oligonucleotide amplicons of a target region, said method comprising: (a) introducing to a sample: (i) a set of primers comprising a first forward primer (FP1), a second forward primer (FP2), and a reverse primer (RP), wherein FP2 is downstream of FP1; wherein the ratio of FP1:FP2:RP is (1-10):(20-200):(1-20); (ii) a solution comprising one or more enzymes, dNTPs, one or more buffering reagents, one or more salts, and one or more crowding reagents; and (iii) a reporter probe; and (b) incubating the sample with the primers and solution at a reaction temperature for a length of time; wherein the method produces single-stranded oligonucleotide amplicons according to a sequence comprising at least a portion of a complementary sequence of the RP and a sequence extending from and including at least a portion of the FP2; wherein the method quantifies the single-stranded oligonucleotide amplicons produced when the single-stranded oligonucleotide amplicons bind to the reported probe.

Embodiment 2C: The method of embodiment 1C, wherein the ratio of FP1:FP2:RP is 1:(50-100):3.

Embodiment 3C: A method of real time asymmetric semi-nested isothermal nucleotide amplification (ANINA) for producing and quantifying single-stranded oligonucleotide amplicons of a target region, said method comprising: (a) introducing to a sample: (i) a set of primers comprising a reverse primer (RP1), a second reverse primer (RP2) and a forward primer (FP), wherein RP2 is upstream of RP1; wherein the ratio of RP1-RP2:FP1 is (1-10):(20-200):(1-20); (ii) a solution comprising one or more enzymes, dNTPs, one or more buffering reagents, one or more salts, and one or more crowding reagents; and (iii) a reporter probe; and (b) incubating the sample with the primers and solution at a reaction temperature for a length of time; wherein the method produces single-stranded oligonucleotide amplicons according to a sequence comprising at least a portion of a complementary sequence of the FP and a sequence extending from and including at least a portion of the RP2: wherein the method quantifies the single-stranded oligonucleotide amplicons produced when the single-stranded oligonucleotide amplicons bind to the reported probe.

Embodiment 4C: The method of embodiment 1C, wherein the ratio of RP1:RP2:FP is 1:(50-100):3.

Embodiment 5C: The method of any one of embodiments 1C-4C, wherein the one or more enzymes comprises a recombinase enzyme, a strand displacing polymerase, a reverse transcriptase, or a combination thereof.

Embodiment 6C: The method of embodiment 5C, wherein the recombinase enzyme is RecA.

Embodiment 7C: The method of embodiment 5C, wherein the strand displacing polymerase is *Bacillus subtilis* DNA polymerase I (Bsu). Bst, or Klenow Fragment.

Embodiment 8C: The method of any one of embodiments 1C-7C, wherein the buffering reagents are Tris, PBS, or a combination thereof.

Embodiment 9C: The method of any one of embodiments 1C-8C, wherein the one or more salts is magnesium acetate ($Mg(C_2H_2O_2)_2$.

Embodiment 10C: The method of any one of embodiments 1C-9C, wherein the one or more salts is magnesium acetate ($Mg(C_2H_2O_2)_2$ and one or a combination of: sodium chloride (NaCl), potassium chloride (KCl), magnesium chloride (MgCl2), sodium acetate ($NaCH_2COO$), monosodium phosphate (NaH2PO4), and disodium phosphate (NA2PO4).

Embodiment 11C: The method of any one of embodiments 1C-10C, wherein the one or more crowding reagents comprises polyvinylpyrrolidone (PVP).

Embodiment 12C: The method of any one of embodiments 1C-11C, wherein the one or more crowding reagents comprises polyvinylpyrrolidone (PVP) and one or a combination of: polyethylene glycol (PEG), Ficoll, and Dextran.

Embodiment 13C: The method of any one of embodiments 1C-12C, wherein the solution further comprises a single stranded binding protein (SSB).

Embodiment 14C: The method of embodiment 13C, wherein the SSB is T4 gp32 SSB.

Embodiment 15C: The method of embodiment 13C, wherein the SSB is *E. coli* SSB (EcSSB).

Embodiment 16C: The method of embodiment 13C, wherein the SSB is *Bacillus subtilis* DNA polymerase I (Bsu).

Embodiment 17C: The method of any one of embodiments 1C-16C, wherein the solution further comprises a reducing agent.

Embodiment 18C: The method of embodiment 17C, wherein the reducing agent is dithiothreitol (DTT), tris(2-carboxyethyl)phosphine (TCEP), or a combination thereof.

Embodiment 19C: The method of any one of embodiments 1C-18C, wherein the reporter probe is a fluorescent probe.

Embodiment 20C: The method of any one of embodiments 1C-18C, wherein the reporter probe is a redox reporter.

As used herein, the term 'about' refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase 'comprising' includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of asymmetric semi-nested isothermal nucleotide amplification for producing single-stranded oligonucleotide amplicons comprising a target region of a template nucleic acid molecule, said method comprising:

a) introducing to a sample comprising the template nucleic acid molecule:
    i) a set of primers comprising:
      A) a first primer (P1) comprising a first template nucleotide sequence, wherein the entire first template nucleotide sequence is complementary to a first complementary binding region (CSBR1), wherein said P1 is 5' to the target region, and wherein said CSBR1 is on a strand opposite to the target region;
      B) a second primer (P2) comprising a second template nucleotide sequence, wherein the entire second template nucleotide sequence is complementary to a second complementary binding region (CSBR2), wherein P2 is (i) 5' to the target region or (ii) 5' to the target region and comprises a portion of the target region, wherein said CSBR2 is on a strand opposite to the target region, and wherein P1 is at least partially 5' to P2; and C) a third primer (P3) comprising a third template nucleotide sequence, wherein the entire third template nucleotide sequence is complementary to a target strand binding region (TSBR) of the target strand, wherein the TSBR comprises (i) at least a portion of the target region, (ii) a portion 3' to the target region, or (iii) any combination of (i) and (ii),
      wherein the ratio of P1:P2:P3 in the set of primers is (1-10):(10-200):(1-20); and
    ii) a solution comprising one or more enzymes, one or more dNTPs, and a buffer, wherein the buffer comprises one or more buffering reagents, one or more salts, and one or more crowding reagents;
  b) incubating the sample with the set of primers and the solution at a reaction temperature for a length of time; and
  c) producing single-stranded oligonucleotide amplicons having a sequence comprising at least the target region of the template nucleic acid molecule.

2. The method of claim 1, wherein the ratio of P1:P2:P3 in the set of primers is 1:(10-200):10.

3. The method of claim 1, wherein the target region is from 20 to 500 bases in length.

4. The method of claim 1, wherein the buffer further comprises a reducing agent.

5. The method of claim 1, wherein the one or more enzymes comprise a recombinase enzyme, a single strand binding protein, a strand displacing polymerase, a reverse transcriptase, or a combination thereof.

6. The method of claim 5, wherein the recombinase enzyme is RecA, Rad51, or RadA.

7. The method of claim 5, wherein the single-stranded binding protein is *Escherichia coli* single-stranded DNA binding protein (EcSSB) or T4 GP32.

8. The method of claim 5, wherein the strand displacing polymerase is *Bacillus subtilis* DNA polymerase I (Bsu), or mesophilic DNA polymerase.

9. The method of claim 1, wherein the one or more buffering reagents are tris(hydroxymethyl)aminomethane (Tris), phosphate buffered saline (PBS), or a combination thereof.

10. The method of claim 1, wherein the one or more salts comprise sodium chloride (NaCl), potassium chloride (KCl), magnesium chloride (MgCl$_2$), sodium acetate (CH$_3$COONa), magnesium acetate (Mg(CH$_3$COO)$_2$), monosodium phosphate (NaH$_2$PO$_4$), disodium phosphate (Na$_2$HPO$_4$), or a combination thereof.

11. The method of claim 1, wherein the one or more crowding reagents are polyvinylpyrrolidone (PVP), polyethylene glycol (PEG), polysucrose, Dextran, or a combination thereof.

12. The method of claim 1, wherein the reaction temperature ranges from 15° C. to 60° C.

13. The method of claim 1, wherein the length of time is from 5 to 60 minutes.

14. The method of claim 1, wherein the buffer has a pH ranging from 7.0-8.0.

15. The method of claim 1, further comprising detecting the target region.

16. The method of claim 15, wherein detection of the target region comprises introducing a genosensor probe.

17. A method of real time asymmetric semi-nested isothermal nucleotide amplification (ANINA) for producing and quantifying single-stranded oligonucleotide amplicons comprising a target region of a template nucleic acid molecule, said method comprising:

a) introducing to a sample comprising the template nucleic acid molecule:

i) a set of primers comprising:

A) a first primer (P1) comprising a first template nucleotide sequence, wherein the entire first template nucleotide sequence is complementary to a first complementary binding region (CSBR1), wherein said P1 is 5' to the target region, and wherein said CSBR1 is on a strand opposite to the target region;

B) a second primer (P2) comprising a second template nucleotide sequence, wherein the entire second template nucleotide sequence is complementary to a second complementary binding region (CSBR2), wherein P2 is (i) 5' to the target region or (ii) 5' to the target region and comprises a portion of the target region, wherein said CSBR2 is on a strand opposite to the target region, and wherein P1 is at least partially 5' to P2;

C) a third primer (P3) comprising a third template nucleotide sequence, wherein the entire third template nucleotide sequence is complementary to a target strand binding region (TSBR) of the target strand, wherein the TSBR comprises (i) at least a portion of the target region, (ii) a portion 3' to the target region, or (iii) any combination of (i) and (ii), wherein the ratio of P1:P2:P3 in the set of primers is (1-10):(10-200):(1-20); and ii) a solution comprising one or more enzymes, one or more dNTPs, and a buffer, wherein the buffer comprises one or more buffering reagents, one or more salts, and one or more crowding reagents;

b) incubating the sample with the set of primers and the solution at a reaction temperature for a length of time; and c) producing single-stranded oligonucleotide amplicons having a sequence comprising at least the target region of the nucleic acid molecule;

wherein the method quantifies the single-stranded oligonucleotide amplicons produced when the single-stranded oligonucleotide amplicons bind to a reporter probe.

18. The method of claim 17, wherein the one or more enzymes comprises a recombinase enzyme, a strand displacing polymerase, a reverse transcriptase, or a combination thereof.

19. The method of claim 18, wherein the recombinase enzyme is RecA, Rad51, or RadA.

20. The method of claim 18, wherein the strand displacing polymerase is *Bacillus subtilis* DNA polymerase I (Bsu), Bst, or Klenow Fragment.

21. The method of claim 17, wherein the one or more buffering reagents are tris(hydroxymethyl)aminomethane (Tris), phosphate buffered saline (PBS), or a combination thereof.

22. The method of claim 17, wherein the one or more salts is magnesium acetate ($Mg(C_2H_2O_2)_2$) or one or a combination of: sodium chloride (NaCl), potassium chloride (KCl), magnesium chloride ($MgCl_2$), sodium acetate ($CH_3COONa$), monosodium phosphate ($NaH_2PO_4$), and disodium phosphate ($Na_2HPO_4$).

23. The method of claim 17, wherein the one or more crowding reagents comprise polyvinylpyrrolidone (PVP) and one or a combination of: polyethylene glycol (PEG), polysucrose, and Dextran.

24. The method of claim 17, wherein the solution further comprises a single stranded binding protein (SSB).

25. The method of claim 24, wherein the SSB is T4 gp32 SSB, *E. coli* SSB (EcSSB), or *Bacillus subtilis* DNA polymerase I (Bsu).

26. The method of claim 17, wherein the solution further comprises a reducing agent.

27. The method of claim 17, wherein the sample is in a second buffer comprising 20 mM phosphate buffered saline (PBS), 2.5 mM ethylenediaminetetraacetic acid (EDTA), and 0.05% sodium dodecyl sulfate (SDS).

* * * * *